United States Patent [19]
Ocali et al.

[11] Patent Number: 5,928,145
[45] Date of Patent: *Jul. 27, 1999

[54] METHOD OF MAGNETIC RESONANCE IMAGING AND SPECTROSCOPIC ANALYSIS AND ASSOCIATED APPARATUS EMPLOYING A LOOPLESS ANTENNA

[75] Inventors: Ogan Ocali, Baltimore; Ergin Atalar, Columbia, both of Md.

[73] Assignee: The Johns Hopkins University, Baltimore, Md.

[*] Notice: This patent issued on a continued prosecution application filed under 37 CFR 1.53(d), and is subject to the twenty year patent term provisions of 35 U.S.C. 154(a)(2).

[21] Appl. No.: 08/638,934

[22] Filed: Apr. 25, 1996

[51] Int. Cl.$^6$ ........................................... A61B 5/055
[52] U.S. Cl. .................... 600/410; 600/411; 600/423; 324/307; 324/309; 324/318
[58] Field of Search ............................. 128/653.2, 653.5; 324/307, 309, 318, 322; 600/410, 411, 423

[56] References Cited

U.S. PATENT DOCUMENTS

| | | | |
|---|---|---|---|
| 4,672,972 | 6/1987 | Berke | 128/653 |
| 4,766,381 | 8/1988 | Conturo et al. | 324/309 |
| 4,776,341 | 10/1988 | Bachus et al. | 128/653.5 |
| 4,922,204 | 5/1990 | Duerr et al. | 324/322 |
| 4,932,411 | 6/1990 | Fritschy et al. | 128/653 A |
| 5,170,789 | 12/1992 | Narayan et al. | 128/653.5 |
| 5,323,778 | 6/1994 | Kandarpa et al. | 128/653.2 |
| 5,358,515 | 10/1994 | Hürter et al. | 607/101 |
| 5,413,104 | 5/1995 | Buijs et al. | 128/653.5 |
| 5,419,325 | 5/1995 | Dumoulin et al. | 128/653.2 |
| 5,437,277 | 8/1995 | Dumoulin et al. | 128/653.1 |
| 5,447,156 | 9/1995 | Dumoulin et al. | 128/653.2 |
| 5,699,801 | 12/1997 | Atalar et al. | 128/653.2 |

FOREIGN PATENT DOCUMENTS

| 06070902 | 3/1994 | Japan | A61B 5/055 |
|---|---|---|---|

OTHER PUBLICATIONS

Atalar, E., et al., "A Flexible Catheter Coil for Imaging and Spectroscopy of Atherosclerotic Plaques," *Society of Magnetic Resonance,* 3rd Meeting, vol. 2, p. 988 (1995).

McKinnon et al., "Towards Visible Guidewire Antennas for Interventional MRI," *Proc. Soc. Mag. Res.,* vol. 1, p. 429 (Aug. 1994).

Spears et al., "In Vivo Coronary Angioscopy," *Journal of the American College of Cardiology,* vol. 1, pp. 1311–1314 (1983).

(List continued on next page.)

*Primary Examiner*—Ruth S. Smith
*Attorney, Agent, or Firm*—Kirk D. Houser; Arnold B. Silverman; Eckert Seamans Cherin & Mellott, LLC

[57] ABSTRACT

The invention provides a method for magnetic resonance imaging and spectroscopic analysis of a specimen which includes positioning the specimen within a main magnetic field and introducing an antenna having a loopless antenna portion in close proximity to the specimen. Radio frequency pulses are provided to the region of interest to excite magnetic resonance signals, gradient magnetic pulses are applied to the region of interest with the antenna receiving magnetic resonance signals and emitting responsive output signals. A processor processes the responsive output signals to provide image information for display in a desired manner. The method in a preferred form involves employing a flexible antenna. The method in another preferred form involves employing an impedance matching circuit electrically interposed between the loopless antenna and the processor to enhance radio frequency power transfer and magnetic resonance signal-to-noise ratio from the loopless antenna to the processor. The method may be used on a wide variety of specimens and in a preferred use is introduced into small blood vessels of a patient to facilitate determination of atherosclerotic plaque. Medical intervention procedures, such as plaque removal, may be employed generally simultaneously with the imaging of the present invention. Corresponding apparatus and magnetic resonance antenna assembly are provided.

73 Claims, 9 Drawing Sheets

OTHER PUBLICATIONS

Waller et al., "Intravascular Ultrasound: A Histological Study of Vessels During Life," *Circulation* vol. 85, pp. 2305–2310 (1992).

Pearlman et al., "Nuclear Magnetic Resonance Microscopy of Atheroma in Human Coronary Arteries," *Angiology*, vol. 42, pp. 726–733 (1991).

Asdente et al., "Evaluation of Atherosclerotic Lesions Using NMR Microimaging," *Atherosclerosis*, vol. 80, pp. 243–253 (1990).

Merickel et al., "Identification and 3–D Quantification of Atherosclerosis Using Magnetic Resonance Imaging," *Comput. Biol. Med.*, vol. 18, No. 2, pp. 89–102 (1988).

Merickel et al., "Noninvasive Quantitative Evaluation of Atherosclerosis Using MRI and Image Analysis," *Atherosclerosis and Thrombosis*, vol. 13, pp. 1180–1186 (1993).

Yuan et al., "Techniques for High–Resolution MR Imaging of Atherosclerotic Plaque," *J. Magnetic Resonance Imaging*, vol. 4, pp. 43–49 (1994).

Vinitski et al., "Magnetic Resonance Chemical Shift Imaging and Spectroscopy of Atherosclerotic Plaque," *Investigative Radiology*, vol. 26, pp. 703–714 (1991).

Maynor et al., "Chemical Shift Imaging of Atherosclerosis at 7.0 Tesla," *Investigative Radiology*, vol. 24, pp. 52–60 (1989).

Mohiaddin et al., "Chemical Shift Magnetic Resonance Imaging of Human Atheroma," *Br. Heart. J.*, vol. 62, pp. 81–89 (1989).

Dumoulin et al., "Real–Time Position Monitoring of Invasive Devices Using Magnetic Resonance," *Magnetic Resonance in Medicine*, vol. 29, pp. 411–415 (Mar. 1993).

Abstract, Koechli et al., "Catheters and Guide Wires for Use in an Echo–planar MR Fluoroscoy System," RSNA 79th Scientific Meeting, *Radiology*, vol. 189(P), p. 319 (Nov. 1993).

Kantor et al., "In Vivo $^{31}$P Nuclear Magnetic Resonance Measurements in Canine Heart Using a Catheter–Coil," *Circulation Research*, vol. 55, pp. 261–266 (Aug. 1984).

Martin et al., "MR Imaging of Blood Vessels with an Intravascular Coil," *J. Magn. Reson. Imaging*, vol. 2, pp. 421–429 (1992).

Hurst et al., "Intravascular (Catheter) NMR Receiver Probe: Preliminary Design Analysis and Application to Canine Iliofemoral Imaging," *Magn. Reson. Med.*, vol. 24, pp. 343–357 (Apr. 1992).

Martin et al., "Intravascular MR Imaging in a Porcine Animal Model," *Magn. Reson. Med.*, vol. 32, pp. 224–229 (Aug. 1994).

Abstract, McDonald et al., "Performance Comparison of Several Coil Geometries for Use in Catheters," RSNA 79th Scientific Meeting, *Radiology*, vol. 189(P), p. 319 (Nov. 1993).

METHOD OF MAGNETIC RESONANCE IMAGING AND SPECTROSCOPIC ANALYSIS AND ASSOCIATED APPARATUS EMPLOYING A LOOPLESS ANTENNA

BACKGROUND OF THE INVENTION

1. Field of the Invention

The present invention relates to an improved method and apparatus for magnetic resonance imaging and spectroscopic analysis of a wide variety of specimens and is in one embodiment employable with small blood vessels in determining the presence of atherosclerotic plaque and the composition thereof.

2. Description of the Prior Art

The advantageous use of magnetic resonance technology in providing safe, rapid images of a patient has long been known. It has also been known to employ magnetic resonance technology in producing chemical shift spectra to provide information regarding the chemical content of a material.

In a general sense, magnetic resonance imaging involves providing bursts of radio frequency energy on a specimen positioned within a main magnetic field in order to induce responsive emission of magnetic radiation from the hydrogen nuclei or other nuclei. The emitted signal may be detected in such a manner as to provide information as to the intensity of the response and the spatial origin of the nuclei emitting the responsive magnetic resonance signal. In general, imaging may be performed in a slice or plane, in multiple planes, or in a three-dimensional volume with information corresponding to the responsively emitted magnetic radiation being received by a computer which stores the information in the form of numbers corresponding to the intensity of the signal. The pixel value may be established in the computer by employing Fourier Transformation which converts the signal amplitude as a function of time to signal amplitude as a function of frequency. The signals may be stored in the computer and may be delivered with or without enhancement to a video screen display, such as a cathode-ray tube, for example, wherein the image created by the computer output will be presented through black and white presentations varying in intensity, or through color presentations varying in hue and intensity. See, generally, U.S. Pat. No. 4,766,381.

One of the beneficial end uses of the present invention is in connection with atherosclerotic disease which is a major cause of mortality and morbidity in the United States. Localized forms of the disease, such as the deposit of plaque on the walls of blood vessels, can restrict local blood flow and require surgical intervention in some instances. While angiography is an effective means for detecting the luminal narrowing caused by plaque, it does not provide information regarding the nature of the process leading to blood flow reduction. Unfortunately, therapeutic methods, such as intravascular intervention, may experience failure due to the lack of sufficiently precise imaging methods. An imaging system capable of providing detailed, qualitative and quantitative data regarding the status of vascular walls at the time of surgical intervention, could favorably influence the outcome by enabling the selection of the intervention method to be customized to the particular need. It would also serve to provide precise guidance for various forms of localized therapy.

It has been known to use angioplasty and intravascular ultrasound for imaging plaques. See, generally, Spears et al., "In Vivo Coronary Angioscopy," *Journal of the American College of Cardiology*, Vol. 1, pp. 1311–14 (1983); and Wailer et al., "Intravascular Ultrasound: A Histological Study of Vessel During Life," *Circulation*, Vol. 85, pp. 2305–10 (1992). Intravascular ultrasound, however, provides several drawbacks, including the insensitivity to soft tissue and the inability to reliably detect thrombus and discriminate thrombus (new or organized) superimposed upon plaque from soft lipid-laden plaques. Also, the presence of artifacts related to transducer angle relative to the vessel wall, and an imaging plane limited to the aperture of the transducer in variable resolution at different depths of view are further problems with this approach.

The feasibility of identification of atherosclerotic lesions by employing magnetic resonance (MR) microimaging in vitro has previously been suggested. See, for example, Pearlman et al., "Nuclear Magnetic Resonance Microscopy of Atheroma in Human Coronary Arteries," *Angiology*, Vol. 42, pp. 726–33 (1991); Asdente et al., "Evaluation of Atherosclerotic Lesions Using NMR Microimaging," *Atherosclerosis*, Vol. 80, pp. 243–53 (1990); and Merickel et al., "Identification and 3-d Quantification of Atherosclerosis Using Magnetic Resonance Imaging," *Comput. Biol. Med.*, Vol. 18, pp. 89–102 (1988).

It has also been suggested that MRI can be used for quantification of atherosclerosis. See, generally, Merickel et al., "Noninvasive Quantitative Evaluation of Atherosclerosis Using MRI and Image Analysis," *Arteriosclerosis and Thrombosis*, Vol. 13, pp. 1180–86 (1993).

Yuan et al., "Techniques for High-Resolution MR Imaging of Atherosclerotic Plaques," *J. Magnetic Resonance Imaging*, Vol. 4, pp. 43–49 (1994) discloses a fast spin echo MR imaging technique to image atherosclerotic plaques on an isolated vessel that has been removed by carotid endarterectomy. As the signal-to-noise ratio (SNR) decreases with the decrease in imaging time and increase in resolution, special radio frequency (RF) receiver coils were designed. The article suggests that by the use of special MR hardware at 1.5 T using various T1 and T2-weighted pulse sequences, it is possible to discriminate foam cells, fibrous plaque organized thrombus, new thrombus, loose necrosis and calcium.

It has also been suggested that the fat content of atherosclerotic plaque in excised tissue samples can be determined using chemical shift imaging or chemical shift spectroscopy. See, generally, Vinitski et al., "Magnetic Resonance Chemical Shift Imaging and Spectroscopy of Atherosclerotic Plaque," *Investigative Radiology*, Vol. 26, pp. 703–14 (1991); Maynor et al., "Chemical Shift Imaging of Atherosclerosis at 7.0 Tesla," *Investigative Radiology*, Vol. 24, pp. 52–60 (1989); and Mohiaddin et al., "Chemical Shift Magnetic Resonance Imaging of Human Atheroma," *Br. Heart J.*, Vol. 62, pp. 81–89 (1989).

The foregoing prior art articles in the aggregate could lead one skilled in the art to conclude that MR, while having potential for fully characterizing vessel wall disease, suffers from low anatomic resolution unless used in vitro on small specimens with high resolution methods.

It is known that in order to obtain the desired high-resolution imaging and spectroscopy of arteriosclerotic plaques, a coil can be placed close to the target blood vessel.

In Kantor et al., "In vivo $^{31}$P Nuclear Magnetic Resonance Measurements in Canine Heart Using a Catheter-Coil," *Circulation Research*, Vol. 55, pp. 261–66 (Aug. 1984), there is disclosed an effort to improve the SNR in the $^{31}$P spectroscopy of a dog myocardium using an elliptical coil. This coil is rigid, rather bulky, and designed for spectroscopy of the myocardium, but is not ideal for vessels.

Disclosures of efforts to develop catheter coils for imaging vessel walls are contained in Martin et al., "MR Imaging of Blood Vessel with an Intravascular Coil," *J. Magn. Reson. Imaging*, Vol. 2, pp. 421–29 (1992); and Hurst et al., "Intravascular (Catheter) NMR Receiver Probe: Preliminary Design Analysis and Application to Canine Iliofemoral Imaging," *Magn. Reson. Med.*, Vol. 24, pp. 343–57 (April 1992). These disclosures employ two tiny diameter, back-to-back solenoid coils to produce a good axial profile when the coils are placed along the main magnetic field.

Martin et al., "Intravascular MR Imaging in a Porcine Animal Model," *Magn. Reson. Med.*, Vol. 32, pp. 224–29 (August 1994) discloses use of the system disclosed in the above-cited Martin et al. article for high-resolution images of live animals. See, also, Abstract, McDonald et al., "Performance Comparison of Several Coil Geometries for Use in Catheters," RSNA 79th Scientific Meeting, *Radiology*, Vol. 189(P), p. 319 (November 1993). A strong disadvantage of these disclosures is that multislice acquisition cannot be carried out because the longitudinal coverage of the sensitive regions is limited to a few millimeters. Furthermore, the coil itself does not have the desired flexibility while maintaining the desired efficiency of data acquisition.

U.S. Pat. No. 5,170,789 discloses a nuclear magnetic resonance (NMR) coil probe, in the form of a loop, that is said to be insertable within a specimen, which has an opening, for purposes of nuclear magnetic resonance spectroscopy (NMRS). The disclosed two component probe, which is in the nature of an endoscope to examine the colon or cervix, has a first portion which is insertable into a body cavity and a second portion which is external to such cavity. The probe has a flexible coil body with an oval or circular shape that may deform during insertion. As a result, the coil may require tuning after insertion. If the coil were made of a very rigid material, insertion problems may occur. Also, a tuning and matching circuit, in the external portion, may limit the depth of insertion.

U.S. Pat. No. 4,932,411 discloses a probe with a transmit/receive coil for insertion in channels which are surgically or otherwise inserted in body organs, such as the brain, liver or kidneys. The coil, which is in the form of a loop, is carried and wound on the distal end of a carrier which is used to insert the coil into the body channel.

U.S. Pat. No. 4,672,972 discloses an NMR probe disposed at the distal end of a catheter or endoscope for obtaining NMR spectra from within a patient. The multi-turn probe has a parametric amplifier and/or a gate-array attached to it and, also, has a coil cooling system.

U.S. Pat. No. 5,413,104 discloses an invasive MRI transducer having a balloon, at least one lumen, and a flexible coil loop for insertion in a body cavity.

It has been known to employ an MR-active invasive device with RF transmitter coils for selective MR angiography of blood vessels. See, generally, U.S. Pat. No. 5,447,156.

It has also been known to employ an intravascular catheter with a Faraday cage to prevent RF energy from acting on fluid, such as blood, and cause the MR signal to be stronger for the fluid exiting the cage. See, generally, U.S. Pat. No. 5,419,325.

MR compatibility characteristics of various catheter and guide wire systems, for use in interventional MR procedures, has been considered. See Dumoulin et al., "Real-time Position Monitoring of Invasive Devices Using Magnetic Resonance," *Magnetic Resonance in Medicine*, Vol. 29, pp. 411–15 (March 1993); and Abstract, Koechli et al., "Catheters and Guide Wires for Use in an Echo-planar MR Fluoroscopy System," RSNA 79th Scientific Meeting, *Radiology*, Vol. 189(P), p. 319 (November 1993).

McKinnon et al., "Towards Visible Guidewire Antennas for Interventional MRI," *Proc. Soc. Mag. Res.*, Vol. 1, p. 429 (August 1994) discloses guidewire antennas which are asserted to promise making Guidewire, biopsy needles and other vascular interventional devices visible by MRI. One MRI stub antenna is a length of coaxial cable with 10 cm of the braid removed from the end. One end of the coaxial cable is directly connected to the surface coil input of an MRI scanner and the other end is placed in a water filled phantom. The MR image is a bright line corresponding to spins in the immediate neighborhood of the cable. A preferred MRI stub antenna is an unterminated twisted pair cable having a diameter of 0.2 or 1 mm, and a corresponding image line width of 1 or 3 mm, respectively, which provides a finer image than the coaxial cable stub antenna. A preferred combination is a steerable guidewire containing a twisted pair cable. It is suggested that a surface coil could be used simultaneously with a guidewire antenna by combining, as with phased array coils, the specimen image from the surface coil with the image of the stub antenna using the data acquired from the stub antenna, to localize the in vivo device during interventional MRI.

It has been known to employ an invasive device having an RF coil for transmitting RF signals which are detected by external RF receive coils to track the invasive device. See, generally, U.S. Pat. No. 5,437,277.

It has also been known to employ external RF transmitter/receiver coils. See, generally, U.S. Pat. No. 5,447,156.

U.S. Pat. No. 5,323,778 discloses a probe for insertion in an artery or other body passageway. The probe has an MRI coil, an external MRI RF source and an RF heating apparatus for hyperthermia therapy.

U.S. Pat. No. 5,358,515 discloses a microwave hyperthermia applicator for limited heating of cancerous tissue including upper and lower dipole halves of the same diameter. The upper dipole half is a widened metal extension of the inner conductor of an insulated coaxial cable. The lower dipole half is a metal cylinder connected to the outer sheath of the coaxial cable. A $\pi/2$ ($\lambda/4$) transformer, such as the outermost metal cylindrical sheath of a triaxial cable, is separated at its upper end from the lower dipole half which is connected to the coaxial cable outer sheath. The transformer is filled with a dielectric medium and is connected at its lower end to such coaxial cable outer sheath. When the antenna is inserted in a dissipative medium and supplied with microwave energy through the coaxial cable, only that area of the medium immediately around the antenna is heated.

MRI has many desirable properties for the diagnosis and therapy of atherosclerotic disease. For example, it is possible to see lesions directly, even before the plaques calcify. However, the SNR of MR images obtained from conventional surface or body coils is insufficient. This is because the coils placed outside the body pick up noise from a very large region of the body. To achieve satisfactory quality, the signal receiver can be placed as close as possible to the tissue of interest (e.g., blood vessels). A coil placed on the tip of a catheter and inserted into the blood vessels could be a solution; but, the real part of the impedance of a catheter coil is relatively small and, hence, a tuning and matching circuit is preferably located immediately after the coil within the blood vessels. It is believed that prior art designs that do otherwise suffer from a significant SNR loss. On the other hand, it is believed that prior art designs, which have a tuning and matching circuit immediately after the coil in blood vessels, are too thick to be placed into small vessels.

There remains, therefore, a very real and substantial need for an improved apparatus and method for MR imaging and spectroscopic analysis of specimens in a manner which provides efficient data acquisition with maximum SNR while permitting in vivo or in vitro acquisition from small vessels and a wide range of other types of specimens.

SUMMARY OF THE INVENTION

As used herein, the term "specimen" shall refer to any object other than a loopless antenna placed in the main magnetic field for imaging or spectroscopic analysis and shall expressly include, but not be limited to members of the animal kingdom, including humans; test specimens, such as biological tissue, for example, removed from such members of the animal kingdom; and inanimate objects or phantoms which may be imaged by magnetic resonance techniques, or which contain water or sources of other sensitive nuclei.

As used herein, the term "loopless antenna" shall expressly include, but not be limited to a dipole antenna and any and all equivalents thereof, such as, for example, a dipole antenna having two poles at least one of which includes a mechanical loop (see, e.g., FIG. 14).

As used herein, the term "patient" shall mean human beings and other members of the animal kingdom.

The present invention has met the above described need.

The method of the present invention includes positioning a specimen within a main magnetic field, introducing an antenna in close proximity to the specimen, employing as the antenna a loopless antenna, imposing the main magnetic field on a region of interest of the specimen, applying radio frequency pulses to the region of interest to excite magnetic resonance signals within the specimen, applying gradient magnetic pulses to the region of interest to spatially encode the magnetic resonance signals with the antenna receiving the magnetic resonance signals and emitting responsive output signals, employing processing means for receiving and processing the responsive output signals and converting them into magnetic resonance information, and employing display means for receiving the magnetic resonance information from the processing means and displaying the same as an image or as chemical shift spectra.

The antenna employed in one preferred embodiment has the loopless antenna and a coaxial cable means structured to be received within the intravascular system, the pancreatic duct, or a tortuous passageway of a patient.

The antenna employed in another preferred embodiment is a loopless antenna structured as a biopsy needle.

The antenna employed in another preferred embodiment has a balancing transformer means operatively associated with a portion of the outer shield of a coaxial cable. For applications within a blood vessel, an insulator in the balancing transformer is preferably employed with a dielectric constant about equal to a dielectric constant of blood in the blood vessel.

The antenna employed in another preferred embodiment has an impedance matching circuit electrically interposed between the loopless antenna and the processing means to enhance radio frequency power transfer and magnetic resonance signal-to-noise ratio from the loopless antenna to the processing means.

The antenna for most embodiments is preferably flexible so as to permit efficient movement through specimen passageways and other specimens or samples to be analyzed regardless of whether the path is straight or not.

The antenna may be employed in chemical shift imaging through acquisition of spatially localized chemical shift information.

In this manner, the method enables both imaging and chemical shift analysis which may also be advantageously employed substantially simultaneously with surgical intervention.

A dipole antenna portion of the loopless antenna may be on the order of about 3 cm to about 20 cm in length, and may have a relatively small maximum outer diameter of about 0.3 mm to about 1.0 cm.

In one embodiment, the antenna also functions as a transmitting antenna to provide the RF signals and, thereby, provide enhanced efficiency of operation for certain uses.

The method may also employ additional elements, such as a balancing transformer and/or an impedance matching circuit in order to provide enhanced operation.

A corresponding magnetic resonance analysis apparatus is provided.

A corresponding magnetic resonance antenna assembly includes an antenna having loopless antenna means at least for receiving magnetic resonance signals emitted from a specimen and emitting responsive output signals.

It is an object of the present invention to provide a method and apparatus for providing high-resolution and spectroscopic imaging of the interior of specimens, including in vivo and in vitro imaging of patients and patient derived specimens or samples.

It is a further object of the present invention to provide such a method and apparatus which will permit rapid imaging of walls of small, tortuous blood vessels with high-resolution, as well as other specimens, and will permit the use of multislice data acquisition techniques.

It is a further object of the present invention to provide such a method generally simultaneously with surgical procedures such as removing plaque from blood vessels.

It is a further object of the present invention to employ a loopless, flexible antenna in such an apparatus to provide both qualitative and quantitative data and to facilitate use of the same substantially simultaneously with medical intervention to correct undesired conditions.

It is a further object of the present invention to provide such an apparatus which facilitates acquiring morphological information about soft tissue and plaque.

It is a further object of the present invention to provide such an apparatus which facilitates acquiring chemical information about soft tissue and plaque.

It is a further object of the present invention to provide such an apparatus wherein the antenna may function only as a receiver antenna or may function as an antenna for both excitation and detection of MR signals.

It is a further object of the present invention to provide such an apparatus wherein the antenna may function as an invasive probe, such as a catheter.

It is a further object of the present invention to provide such an apparatus wherein the antenna may function as a probe-type medical device such as a biopsy needle.

It is a further object of the present invention to provide such an apparatus wherein no tuning or impedance matching circuit is generally required.

It is a further object of the present invention to provide such an apparatus wherein no tuning of the antenna is generally required after such antenna is inserted in a patient.

It is a further object of the present invention to employ an antenna and an impedance matching circuit which may be employed with conventional hardware.

These and other objects of the present invention will be more fully understood from the following description of the invention with reference to the illustration appended hereto.

DESCRIPTION OF THE PREFERRED EMBODIMENTS

Figure 1:
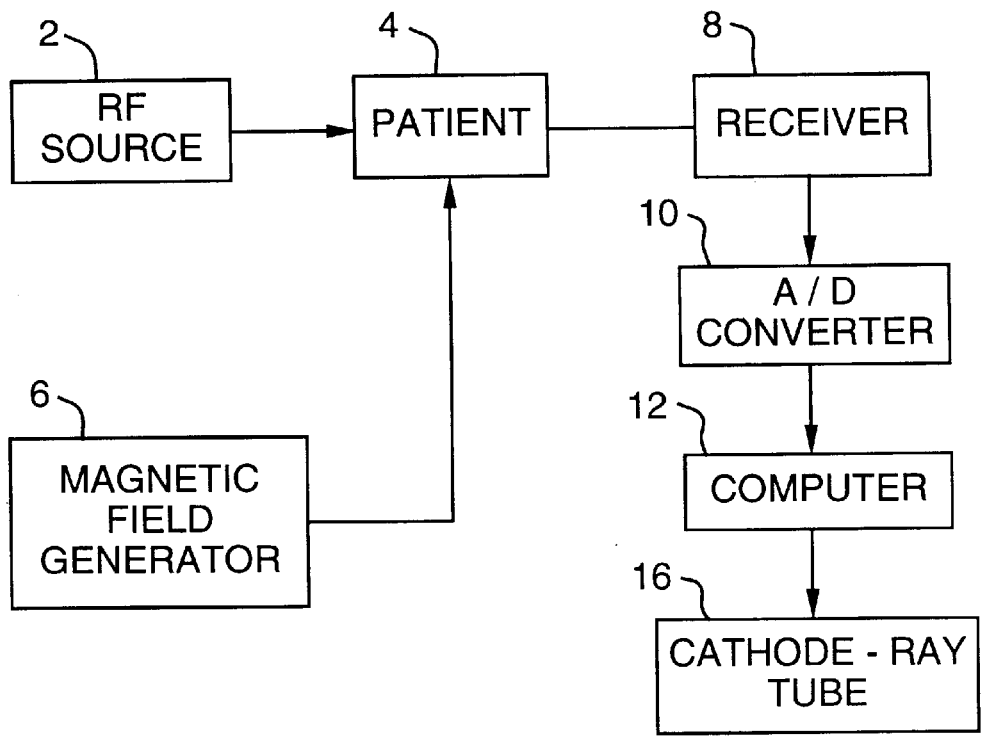
FIG. 1 is a schematic illustration of a magnetic resonance analysis system.

FIG. 1 shows a schematic representation of the general concept of magnetic resonance analysis as employed with a specimen. An RF source 2 provides pulsed radio frequency energy to the specimen to excite MR signals therefrom. The specimen, in the form shown, is a patient 4 disposed in the main magnetic field which is created by a magnetic field generator 6. The generator 6 includes a magnetic field gradient generator for establishing gradients in the main magnetic field by applying gradient magnetic pulses on the region of interest of the patient 4 in order to spatially encode the MR signals.

The exemplary patient 4 is generally aligned with the main magnetic field and the RF pulses are emitted perpendicular thereto to one portion, several portions, or all of the specimen. Where oblique imaging is employed, the angle of impingement of the vector representing the spatial gradient of the magnetic field will be angularly offset from either the x, y, or z directions (not shown). This arrangement results in excitation of the nuclei within the area or volume to be imaged and causes responsive emission of magnetic energy which is picked up by a receiver 8 having a loop antenna (i.e., a receiver coil) in close proximity to the patient 4.

Preferably, the loop antenna of the receiver 8 is aligned with the z direction (i.e., the direction of the main magnetic field) in order to have maximum sensitivity. In the event the loop antenna is perpendicular to the main magnetic field, it has a practically zero sensitivity at certain locations. For oblique angles therebetween, the loop antenna has data acquisition capability, albeit with reduced sensitivity, thereby permitting data acquisition even at oblique angles.

The loop antenna or receiver coil of the receiver 8 has a voltage induced in it as a result of such responsive emissions of magnetic energy. As a practical matter, separate coils or identical coils may be employed by the RF source 2 and receiver 8. The responsive output signal emerging from receiver 8 is amplified, phase-sensitive detected, and passes through analog-to-digital (A/D) convertor 10 and enters a processor, such as computer 12, which receives and processes the signals from the converter 10 and creates MR information related thereto. Within computer 12 the Fourier Transformations of signals convert the plot of amplitude versus time to a map of the distribution of frequencies by plotting amplitude versus frequency. The Fourier Transformations are performed in order to establish the intensity value locations of specific image pixels of the specimen and to obtain chemical shift spectra at those locations. These values may be stored, enhanced or otherwise processed, and emerge to be received and displayed as an image or as chemical shift spectra, as appropriate, on a suitable screen, such as a cathode-ray tube (CRT) 16, for example.

In chemical shift spectra applications, for example, the magnetic field gradient generator of generator 6 generates the magnetic field gradient substantially parallel to the loop antenna of the receiver 8 over the region of interest in order to generate one-dimensional resolved chemical shift spectra which are spatially resolved substantially along the length of the loop antenna on the region of interest. The computer 12 converts spatially localized chemical shift information in the responsive output signals to chemical shift spectra, and employs the CRT 16 to receive and display such spectra. This facilitates one-dimensional chemical shift imaging in which the chemical shift information is spatially resolved in a direction substantially along the length of the loop antenna on the region of interest of the specimen.

Figure 2:
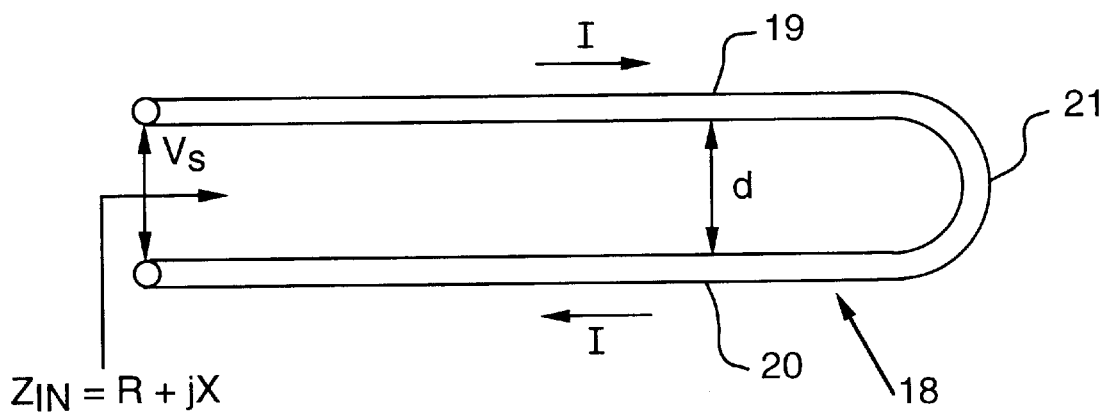
FIG. 2 is a form of a catheter coil for the system of FIG. 1.

Those skilled in the art will appreciate that the transmission properties of a coil may be used to analyze its reception properties. Referring to FIG. 2, in general, the signal voltage $V_S$ of a coil 18 is determined in Equation 1:

$$V_S = \omega \mu H.M \qquad \text{(Eq. 1)}$$

wherein:

ω is 2πF

F is frequency of RF source 2

μ is permeability constant

H is magnetic field (vector) generated by coil 18 at unit input current I

M is sample magnetization (vector)

Of the factors affecting the signal voltage $V_S$, H is the only coil-dependent parameter.

The RMS noise voltage $V_N$ of the coil 18 is determined in Equation 2:

$$V_N = \sqrt{4k_B TRf} \qquad \text{(Eq. 2)}$$

wherein:
$k_B$ is the Boltzman constant
T is sample temperature
R is real part of impedance seen from the terminals of coil 18
$f=2BW/(N_x N_y EX)$ is effective pixel bandwidth
BW is receiver bandwidth
$N_x$ is number of pixels along the readout direction
$N_y$ is number of pixels along the phase encoding direction
NEX is number of averages The only coil-dependent parameter that affects the noise voltage $V_N$ is R.

The signal-to-noise ratio (SNR) is determined in Equation 3:

$$SNR = \frac{V_S}{V_N} \propto \frac{H}{\sqrt{R}} \qquad \text{(Eq. 3)}$$

wherein:
H is magnetic field (value) generated by coil 18 at unit input current I To improve SNR, H should increase and R should decrease. For example, in coils, these are generally conflicting goals. A typical value of R for the coil 18 is about 0.5 Ω.

In the structure of the conventional catheter coil 18, magnetic fields generated by the two conductors 19,20 cancel partially. This cancellation effect becomes more pronounced as the distance of the specimen from the coil 18 increases. In this configuration, the path of the current I is completed by the end conductor 21, which forms an electrical loop or coil with the conductors 19,20. The performance of the coil 18 depends strongly on the separation distance d between the conductors 19,20 and worsens (improves) as such separation decreases (increases).

Figure 3:
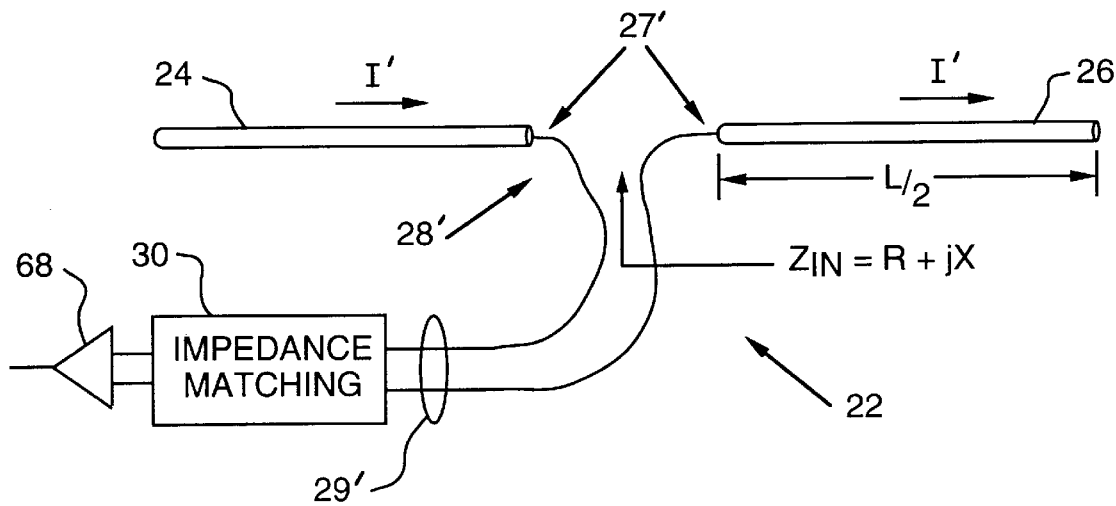
FIG. 3 is a schematic of a loopless antenna and an impedance matching circuit for the system of FIG. 1 in accordance with the present invention.

FIG. 3 illustrates an antenna 22 in accordance with the present invention. The cancellation of the magnetic fields is avoided by separating the conductors 24,26 as schematically shown in FIG. 3. The H field increases considerably by this operation. In this configuration, the path of the current I' is not completed, and charges simply oscillate between the two tips of the antenna 22. The H field generated by the antenna 22 becomes circular thereabout and is approximately inversely proportional with the distance thereto. The antenna 22 includes the conductors 24,26, which form a loopless antenna 27' having a dipole antenna portion 28' and a connection portion 29'; and, in this embodiment, an impedance matching circuit 30. The impedance matching circuit 30 is electrically interposed between the loopless antenna 27' and a preamplifier 68 of the receiver 8 of FIG. 1 and enhances RF power transfer and MR SNR from the antenna 27' to the converter 10 of FIG. 1. The parameters of the impedance matching circuit 30 are chosen to resonate the antenna 27' at the MR frequency of the nuclei of interest and to match the antenna 27' to the optimum input impedance of the preamplifier 68.

Figure 4:
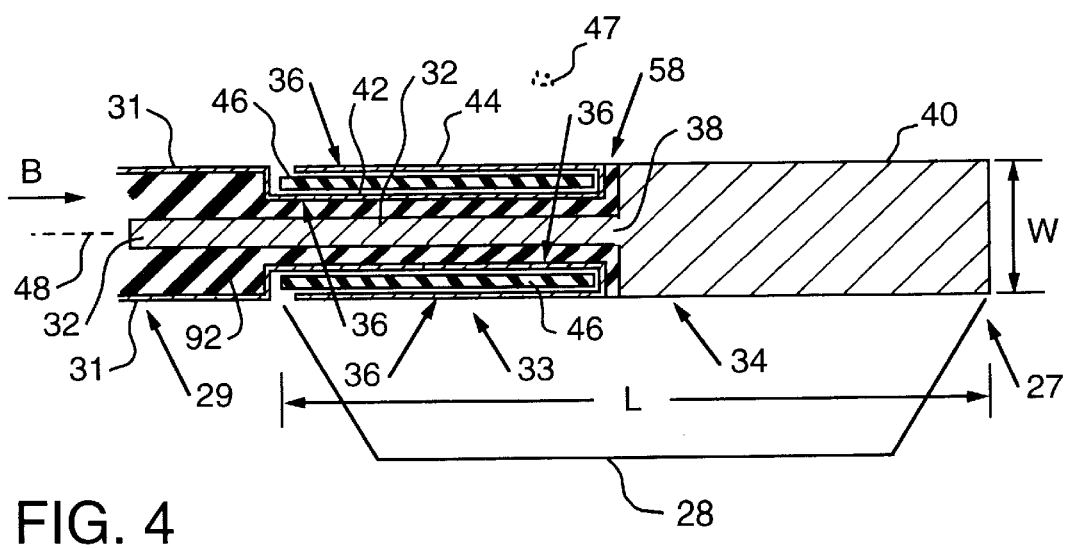
FIG. 4 is a cross-sectional view of a loopless balanced antenna in the present invention.

Referring to FIG. 4, a specific example of the antenna 27' of the invention will be considered.

EXAMPLE 1

FIG. 4 is a cross-sectional view of an exemplary loopless balanced antenna 27. A dipole antenna portion 28 receives MR signals emitted from a specimen responsive to pulsed RF signals and units responsive output signals. A connection portion 29 emits the responsive output signals to the impedance matching circuit 30 of FIG. 3. In this embodiment of the invention, the connection portion 29 is a coaxial cable having an outer primary shield 31 and an inner conductor 32. The coaxial cable 29 is electrically interposed between the dipole antenna portion 28 and the impedance matching circuit 30.

The dipole antenna portion 28 has a first pole 33 and a second pole 34. A portion 36 of the outer shield 31 is operatively associated with the first pole 33. A portion 38 of the inner conductor 32 is operatively associated with the second pole 34. The second pole 34 preferably includes a cylindrical conductor 40 electrically interconnected with the portion 38 of the inner conductor 32.

The portion 36 of the outer shield 31 at the first pole 33 forms an inner primary shield 42 and an outer secondary shield 44, each of which is coaxial with the inner conductor 32. The first pole 33 includes the shields 42,44. In this manner, the secondary shield 44 is also for receiving the MR signals.

The first pole 33 also includes a dielectric coating or insulator 46 under the outer secondary shield 44, between such shield 44 and the inner primary shield 42. The insulator 46 and the shields 42,44 form a balancing transformer operatively associated with the first pole 33. The balancing transformer suitably disables current flow on the outer surface of the primary shield 31, without significantly impeding current flow on the inner surface thereof.

Preferably, the insulator 46 is a relatively high dielectric constant ($\in_r$) insulator having a value of about 70 to about 100. Preferably, for optimal balancing, the dielectric constant of the insulator 46 is selected in order that the length L/2 (as shown in FIG. 3) of the transmission line formed by the primary shield 42 and the secondary shield 44 (as shown in FIG. 4) has a length of λ/4, where λ is the wavelength in the insulator 46 at the MR frequency of nuclei of interest. In this manner, the unbalanced current flowing on the outer surface of the primary shield 31 is greatly reduced.

For applications in vivo in a patient, the $\in_r$ value of the insulator 46 is preferably selected to match the $\in_r$ value of the surrounding medium 47 (e.g., the $\in_r$ value of blood which ranges from about 70 to about 100). For other applications, the antenna 27 is preferably introduced in close proximity to the specimen. The insulator 46 may be made of any insulator having a suitable $\in_r$ value and, preferably, is made of titanium oxide or a composite thereof.

Figure 8:
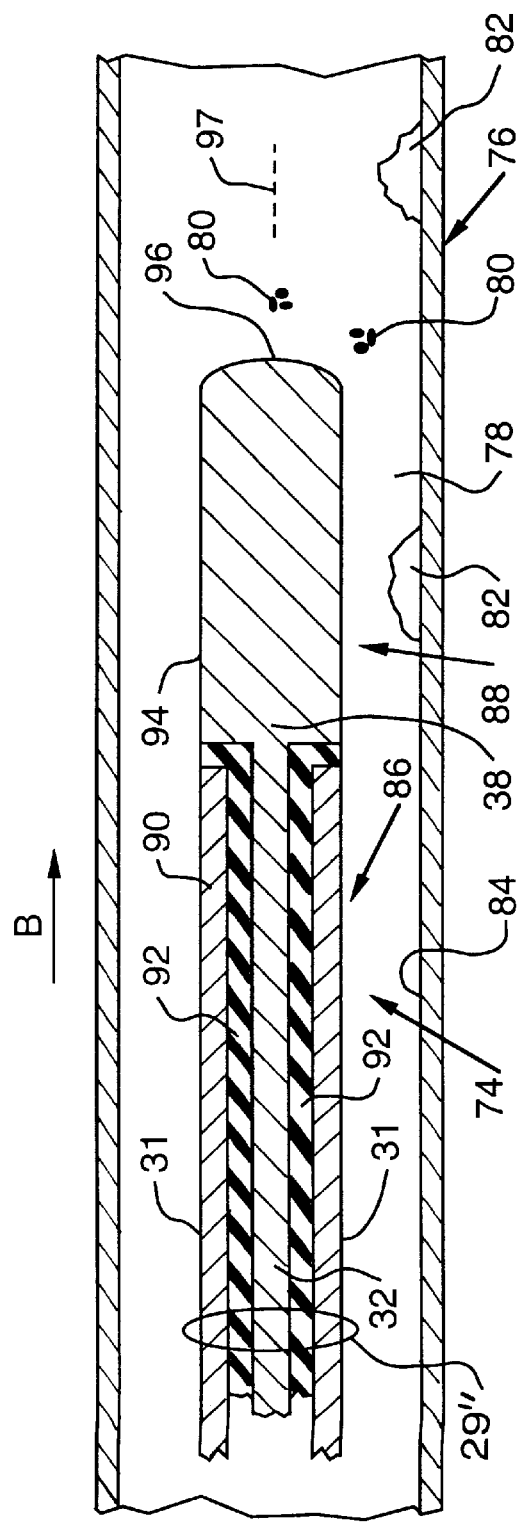
FIG. 8 is a cross-sectional view of a loopless antenna and coaxial cable positioned in a blood vessel.

Preferably, in terms of extending the sensitivity along the length of a loopless antenna, as discussed below in connection with FIG. 8, a balancing transformer is not employed. In the embodiment of FIG. 8, current flows on the outer surface of the primary shield 31 and the noise voltage is higher thereby providing a lower SNR. The primary shield 31 serves to receive the MR signal as well as the portion of the pole 86 which is adjacent the pole 88. However, removing the balancing transformer reduces the SNR slightly.

The balancing transformer of FIG. 4 is preferably employed to avoid unbalanced currents which would otherwise make the input impedance $Z_{IN}$ of FIG. 3 sensitive to changes in loading conditions and the position of the loopless antenna 27.

The inner conductor 32 and the cylindrical conductor 40 may be made of a good non-magnetic, electrical conductor, such as copper, silver, or aluminum, for example. Because of the skin effect, however, wherein only about an 8 μm outer layer of the conductors 32,40 carries electrons at RF frequencies, a material plated with a good conductor will also function effectively. For example, silver plated copper, gold plated copper, or platinum plated copper may be employed.

The dipole antenna portion 28 of the exemplary balanced loopless antenna 27 has a length L of about 3 cm to about 20 cm, with larger (smaller) lengths obtained with smaller (larger) RF frequencies (e.g., less than about 400 MHz), although larger lengths of up to about 2 m are possible with the unbalanced loopless antenna 74 of FIG. 8. The length L facilitates multislice imaging without moving the loopless antenna 27. Preferably, resiliently flexible loopless antennas 27,74 are provided. The optimal length of the antenna 27 at 1.5 T in human tissue is about 7 cm to about 10 cm. The exemplary balanced loopless antenna 27 has a maximum width of about 0.5 mm to about 1.0 cm, although smaller widths of about 0.3 mm are possible with the unbalanced loopless antenna 74 of FIG. 8.

The sensitivity profile of the exemplary antennas 27,74 depends on the respective antenna's orientation with respect to the main magnetic field. The best performance is achieved when the antennas 27,74 are aligned with the main magnetic field. In other words, in order to function effectively, the longitudinal axis 48 is parallel to the main magnetic field B with the poles 33,34 along the length of the loopless antenna 27. For example, for in vivo applications of the antennas 27,74, the patient (and, hence, the antenna therein), may be moved to provide suitable alignment with the direction of the main magnetic field B.

The antennas 27,74 supply a relatively high signal voltage, since there are no magnetic field cancellations as in the coil 18 of FIG. 2. To estimate SNR performance, as shown in Equation 3, the noise resistance R (i.e., the real part of the impedance $Z_{IN}$) is necessary. The input impedance $Z_{IN}$ of the antennas 27,74 may be measured experimentally (e.g., using a vector impedance meter in a saline solution which has conductivity similar to the particular specimen such as mammalian tissue). It is also possible to calculate the input impedance $Z_{IN}$ by solving the associated electromagnetic problem. Both the real (R) and imaginary (jX) parts of the input impedance $Z_{IN}$ are preferably employed in designing the impedance matching circuit 30 of FIG. 3.

Figure 5A:
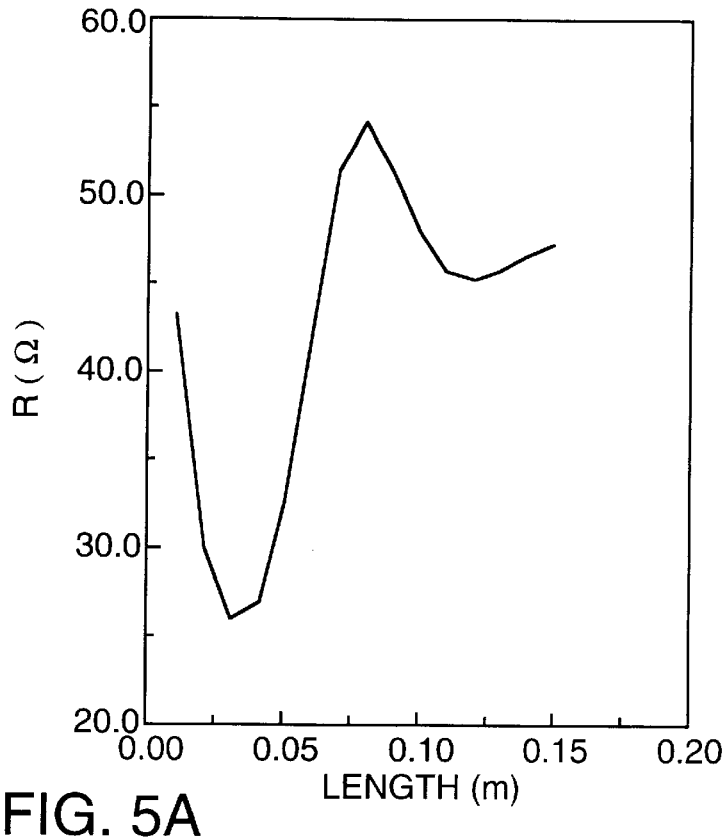
FIGS. 5A–5B are plots of noise resistance with respect to antenna length for a loopless antenna similar to the embodiment of FIG. 4.
Figure 5B:
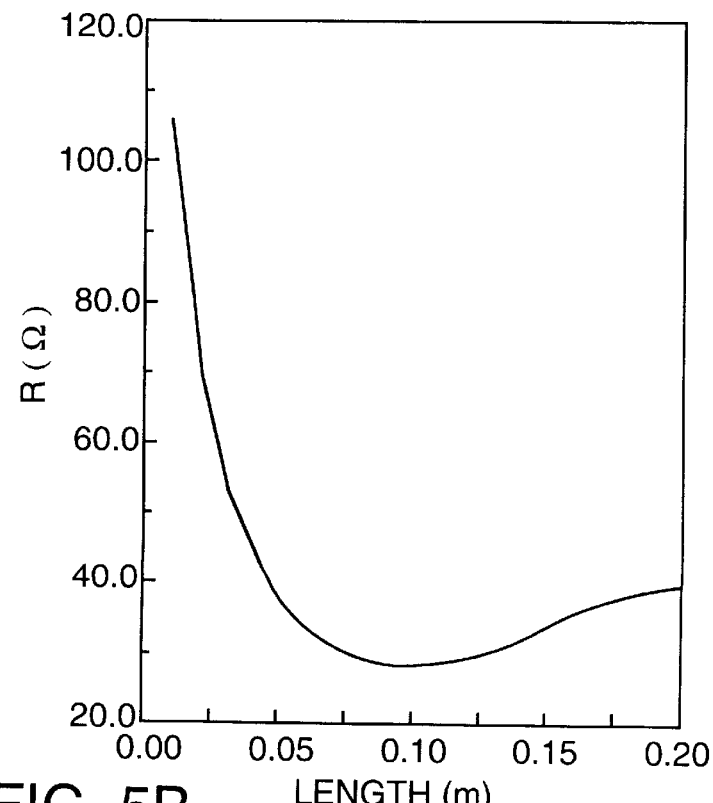

Preferably, for optimal SNR performance, the noise resistance R should be as small as possible. As shown in Figures 5A and 5B, noise resistance R (ohms) is plotted for changing antenna length (meters), for two different exemplary main magnetic field strengths, 4.7 Tesla (T) and 1.5 T, respectively, for a loopless antenna (not shown) similar to the loopless antenna 27 of FIG. 4. The loopless antenna represented by FIGS. 5A and 5B has a diameter of about 1.0 mm and a balancing transformer insulator with a dielectric constant ($\in_r$) representative of human body tissue. In both cases, R attains a shallow minimum (e.g., about 20 Ω to about 30 Ω). Preferably, the length of the loopless antenna is chosen around those minima.

The noise resistance R of the antenna 22 of FIG. 3 weakly depends on the radius of the conductors 24,26. Compared to a typical 0.5 Ω input impedance of the conventional coil 18 of FIG. 2, the noise resistance R of the loopless antenna 27 of FIG. 4 approaches about two orders of magnitude larger and, hence, the noise voltage $V_N$ approaches about one order of magnitude larger (as shown by the square root function of Equation 2). However, the signal voltage $V_S$ of the loopless antenna 27 is also larger. The SNR performances of the coil 18 and the loopless antenna 27 equate at a distance of about 5–8 times the conductor separation distance d for the coil 18.

At smaller distances, the coil 18 is better, but for larger distances the loopless antenna 27 has a better SNR performance.

Figure 6:
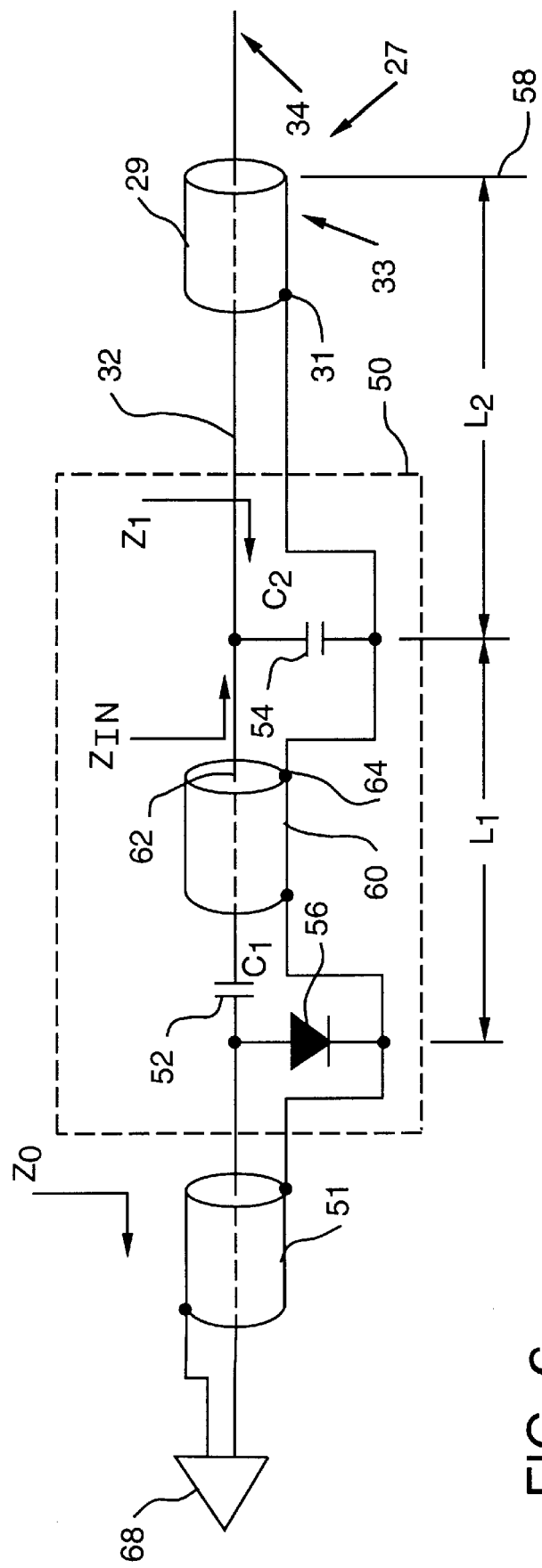
FIG. 6 is a schematic illustration of the loopless antenna of FIG. 4, an impedance matching and decoupling circuit, and a preamplifier.

Referring to FIG. 6, a specific example of the impedance matching circuit 30 of FIG. 3 of the invention will be considered.

EXAMPLE 2

FIG. 6 is a schematic illustration of the loopless antenna 27 of FIG. 4, and a suitable exemplary impedance matching and decoupling circuit 50, although the invention is applicable to a wide variety of impedance matching circuits, and tuning and impedance matching circuits. The loopless antenna 27 is electrically interconnected to the circuit 50 by the coaxial cable 29. The circuit 50 serves to match the impedance of the loopless antenna 27 with the characteristic impedance $Z_o$ of a coaxial cable 51. The coaxial cable 51 is connected to the preamplifier 68 of the receiver 8 of FIG. 1 and carries the MR signal thereto. In this manner, the coaxial cable 51 is electrically interposed between the computer 12 of FIG. 1 and the circuit 50, with such circuit 50 matching the input impedance $Z_{IN}$ of the loopless antenna 27 to the characteristic impedance $Z_o$ of the cable 51.

The loopless antenna 27 has a relatively large noise resistance R, which makes it possible to place the circuit 50 relatively far from the antenna 27 without significant SNR performance degradation. This is an important advantage over the relatively low noise resistance coil 18 of FIG. 2 because, during imaging therewith, the matching circuitry (not shown) thereof is preferably placed inside the specimen to eliminate a significant SNR loss.

The circuit 50 includes a direct current (DC) blocking capacitor 52, a matching capacitor 54, and a PIN diode 56. The matching capacitor 54 is electrically interposed in the circuit 50 between the inner conductor 32 and the outer shield 31 of the coaxial cable 29. The PIN diode 56 is electrically interposed between the DC blocking capacitor 52 and the preamplifier 68. The DC blocking capacitor 52 is electrically interposed between the PIN diode 56 and the inner conductor 32 of the coaxial cable 29. The coaxial cable 29 is preferably structured with a suitable diameter for reception within an intravascular system, whereas the circuit 50 and the coaxial cable 51 may have a larger diameter, although the invention is applicable to a wide variety of impedance matching circuits (e.g., formed from individual discrete components, electronic integrated circuits, other miniaturized circuits).

In receive only mode during RF excitation, RF current may be induced in the antenna 27. In order to resist current induction in the antenna 27 during RF transmission, and obviate resonance of the antenna 27 which may interfere with the flip angle profile, the MR scanner hardware in the RF source 2 of FIG. 1 may provide a positive DC pulse to the antenna 27 for this purpose. The positive DC pulse turns on the PIN diode 56 during RF transmission.

In the exemplary circuit 50, $L_1$ is the distance between PIN diode 56 and the matching capacitor 54, and $L_2$ is the distance between matching capacitor 54 and the point 58 (best shown in FIG. 4) intermediate the poles 33,34 of the loopless antenna 27. The capacitance ($C_2$) of the matching capacitor 54 and the length $L_2$ are chosen such that the input impedance $Z_{IN}$ of the loopless antenna 27 is equal to the characteristic impedance $Z_o$ of the coaxial cable 51. In other words, the length $L_2$ is adjusted in order that when the PIN diode 56 is on, the coaxial cable 29 behaves like an inductor and resonates with the capacitor 54 to disable a current through the loopless antenna 27, although various designs are possible to achieve this desired performance. Then, the length $L_1$ is chosen such that when the PIN diode 56 is turned on, the impedance, $Z_1$, seen by the loopless antenna 27, becomes as large as possible.

In the exemplary embodiment, a substantial portion (i.e., coaxial cable 29) of the length $L_2$ may be inserted within the specimen with the circuit 50 external thereto. The exemplary circuit 50 includes a coaxial cable 60 having a center conductor 62 and outer shield 64. The matching capacitor 54 is electrically interconnected between the center conductor 62 and outer shield 64 at one end of the coaxial cable 60. The DC blocking capacitor 52 is electrically disposed at the other end between the center conductor 62 and the PIN diode 56.

For example, with tap water as the medium, the values of the design parameters are: the capacitance ($C_1$) of the DC blocking capacitor 52 is about 500 pF, $C_2$ is about 70 pF, $L_1$ is about $0.06\lambda$, $L_2$ is about $0.209\lambda$, and $Z_o$ is about 50 $\Omega$, with $\lambda$ being about 2 times the length L of FIG. 4. Regardless of these values, the performance of the circuit 50 is generally not critical since the input impedance $Z_{IN}$ of the loopless antenna 27 is typically of the same order of magnitude as the characteristic impedance of the coaxial cable 51.

An example of an MR scanner usable in the practice of the present invention is the General Electric (G.E.) 1.5 T Signa™ MR scanner, although the invention is applicable to a wide variety of MR scanners having a wide range of main magnetic field strengths. The MR scanner sources RF pulses to a transmitting coil which transmits such RF pulses in order to excite MR signals. As discussed below in connection with FIG. 7, the loopless antenna 27 may also be employed as an RF pulse transmitting source in addition to employment as a receiver antenna.

Preferably, to obviate insertion of any active or passive electronic components in a blood vessel, a $\lambda/2$ cable length, or multiple thereof, is added to the length $L_2$. In this manner, the length of the coaxial cable 29 may be extended by up to about several feet to facilitate MR analysis more deeply within the specimen.

Figure 7:
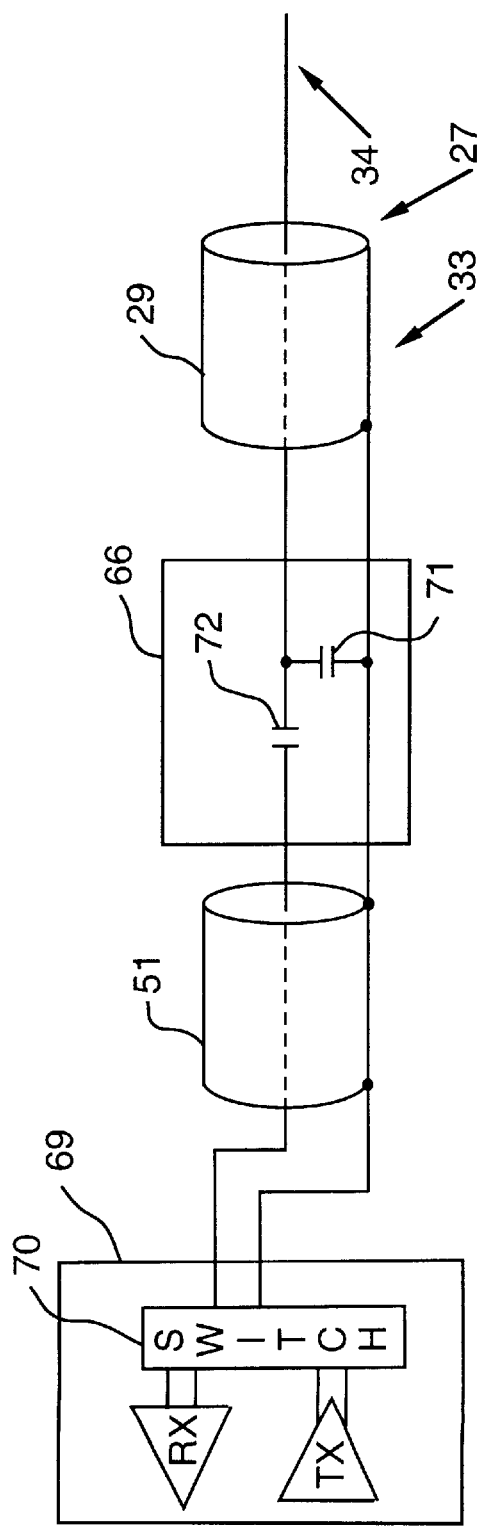
FIG. 7 is a schematic illustration of the loopless antenna of FIG. 4, a matching circuit, two coaxial cables, and a transceiver.

Referring to FIG. 7, another specific example of the impedance matching circuit 30 of FIG. 3 of the invention will be considered.

EXAMPLE 3

FIG. 7 is a schematic illustration of the loopless antenna 27, the coaxial cable 29, an impedance matching circuit 66, the coaxial cable 51, and a transceiver 69. The receiver (RX) portion of the transceiver 67, through the switch portion 70 thereof, is employed to receive the responsive output signals from the loopless antenna 27. For matching at the time of manufacture, matching circuit 66 is provided with capacitors 70,71, which are electrically interconnected to the loopless antenna 27 by the coaxial cable 29. The matching circuit 66 maximizes RF power transfer from the antenna 27 to the RX portion of the transceiver 69 which receives and amplifies the output of the circuit 66. In this embodiment, unlike the embodiment of FIG. 6, there is no PIN diode and the loopless antenna 27 provides a transmitter antenna function as well as a receiver antenna function. The transmitter (TX) portion of the transceiver 67, through the switch portion 70 thereof, is employed to transmit the RF pulses to loopless antenna 27.

The matching circuit 66 is preferably placed nearby the loopless antenna 27, although the length of the coaxial cable 29 may be extended up to about several feet in a similar manner as discussed above in connection with FIG. 6. This is especially advantageous in the case where the loopless antenna 27 and the coaxial cable 29 are employed in the manner of a catheter in vivo. The arrangement of the impedance matching circuit 66 in FIG. 7 is not limiting and it will be understood that other impedance matching, tuning and impedance matching, or impedance matching and decoupling arrangements (e.g., inductor/capacitor, a circuit for shorting the coaxial cable, suitable RF switching circuitry, a coaxial cable having an impedance about equal to the impedance of the loopless antenna) will be evident to those skilled in the art.

Referring to FIG. 8, another specific example of the antenna 27' of FIG. 3 of the invention will be considered.

EXAMPLE 4

FIG. 8 is a cross-sectional view of a loopless antenna 74 and a coaxial cable 29" positioned in an intravascular system such as, for example, within a blood vessel such as a human vein 76. The vein 76 has an interior bore 78 filled with blood 80, and one or more atherosclerotic plaque deposits, such as plaque deposits 82, which are secured to the interior surface 84 of the vein 76. The antenna 74, in the form shown, is connected to the coaxial cable 29" which, in turn, is connected to a suitable circuit, such as the circuit 50 of FIG. 6 or the circuit 66 of FIG. 7, which serves to match the impedance of the antenna 74 with the impedance of the coaxial cable 51 of FIGS. 6 and 7.

The loopless antenna 74 has a first pole 86 and a second pole 88. The cylindrical outer shield 31 of the coaxial cable 29" is electrically insulated from the center conductor 32 of such cable 29" by the dielectric portion 92 thereof. Unlike the antenna 27 of FIG. 4, the antenna 74 does not have a balancing transformer insulator such as insulator 46.

The second pole 88 includes a cylindrical conductor 94 electrically interconnected with the portion 38 of the inner conductor 32. Preferably, for use in a patient, the end 96 of the cylindrical conductor 94 is suitably rounded to obviate damaging the patient (e.g., the interior surface 84 of the vein 76). In this application, the loopless antenna 74 and coaxial cable 29" are employed in the manner of an invasive probe, such as a catheter, with the matching circuit, such as the circuit 50 of FIG. 6 or the circuit 66 of FIG. 7, located external to the vein 76. The exemplary loopless antenna 74 and coaxial cable 29" are elongated along longitudinal axis 97 with a length of up to about 2 m and an external diameter of about 0.3 mm in order to be received within a blood vessel of a patient.

The antenna 74, cable 29" and suitable matching circuit (not shown) are employable to acquire MR image information or MR chemical shift information about atherosclerotic plaques. For example, as discussed above in connection with FIG. 1, the computer 12 converts the responsive output signals from the antenna 74 into MR image information, and the CRT 16 displays the MR image information in order to image the vein 76. It will be appreciated that the cylindrical conductor 94 may alternatively be employed with the antenna 27 of FIG. 4 for high resolution intravascular and other in vivo applications in a patient. It will further be appreciated that the use of the exemplary antenna 74 and cable 29" may be employed generally simultaneous with a medical, surgical, or interventional procedure on the patient, such as removal of the plaque deposits 82 from the vein 76 by a suitable cutting device (not shown).

Insulating the antenna 74 does not change its electrical properties unless the insulation (not shown) is extensively thick (e.g., greater than about 0.1 mm).

It will be appreciated with the present invention that the antennas 27 and 74 of FIGS. 4 and 8, respectively, may be employed, for example, in a blood vessel to provide an image and 1-D spectroscopic analysis of plaque built up on the interior of the vessel wall with multislice imaging being provided in an efficient manner due to such elongated antennas being employed. The antennas 27,74 may also be employed to examine many other characteristics, such as fatty streaks, calcification, sclerosis, and thrombosis, for example. It will further be appreciated that substantially simultaneously with the use of such antennas and coaxial cables 29,29", medical intervention as, for example, by laser therapy or destruction of the undesired plaque, may be employed. Similarly, any normal diagnostic or therapeutic measures undertaken with the aid of an endoscope (not shown), may be accomplished substantially simultaneously with the use of such antennas for imaging and/or spectroscopic analysis.

Figure 9:
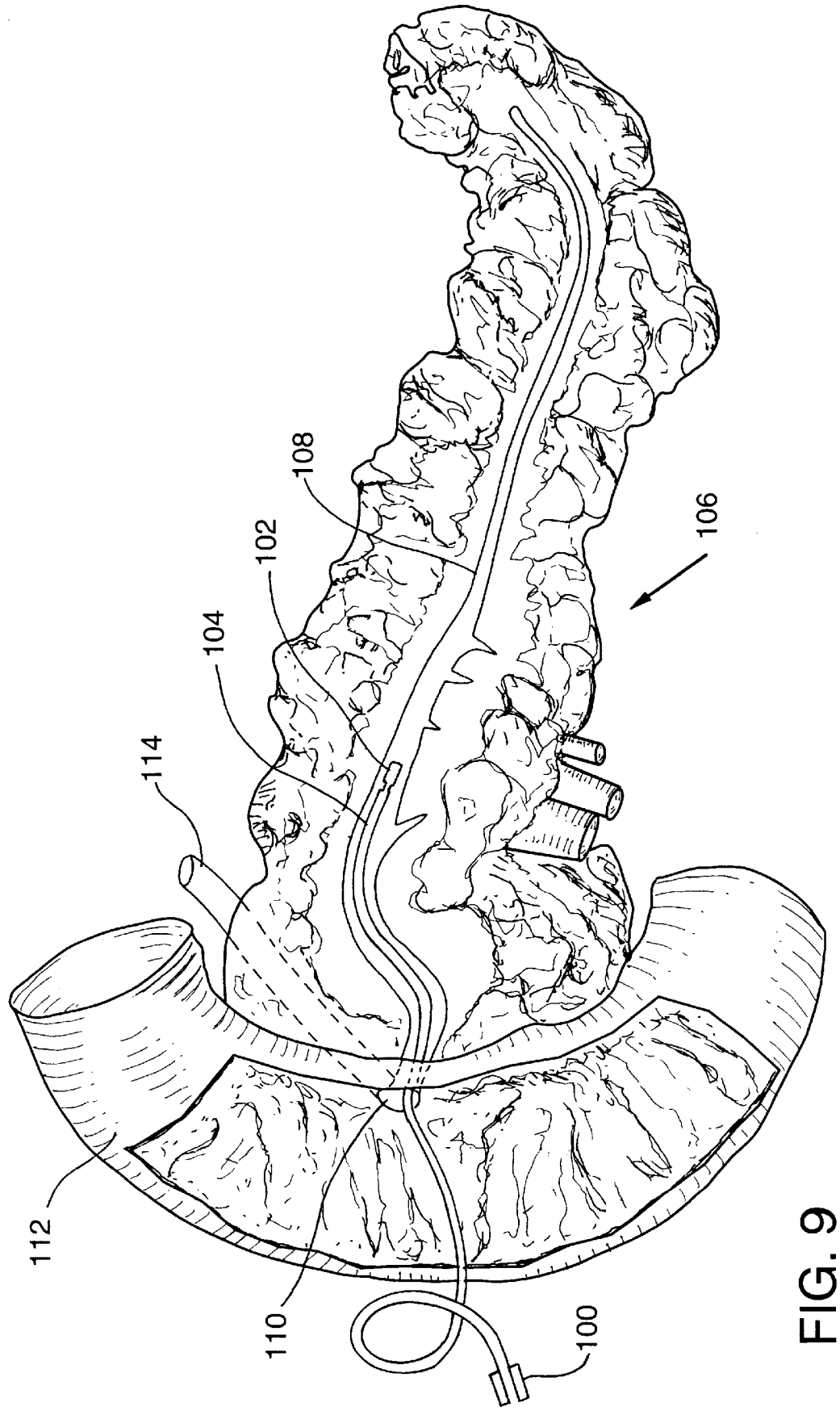
FIG. 9 is a cross-sectional view of a human pancreas with a catheter loopless antenna positioned in the pancreatic duct.

Alternatively, an external dielectric material 100 may be employed as illustrated with the loopless antenna 102 and coaxial cable 104 of FIG. 9 which shows, for consideration, another specific example of the antenna 27' of FIG. 3.

EXAMPLE 5

FIG. 9 is a cross-sectional view of a human pancreas 106 with the antenna 102 and a portion of the coaxial cable 104 positioned in a pancreatic duct 108. The antenna 102 and coaxial cable 104 are employed in the manner of an invasive probe, such as a catheter, during a surgical procedure, associated with the pancreas 106, on the human patient. The antenna 102 and coaxial cable 104 are introduced into the human patient to conduct internal MR analysis thereof.

The antenna 102 and cable 104 have an external diameter which is structured to be received within a naturally occurring passageway in a human being, such as the opening 10 of the pancreatic duct 108. This opening 110, for example, is accessible during surgery on the duodenum 112, although the antenna 102 and cable 104 are structured to be received within a wide variety of naturally open passageways (e.g., bile duct 114, urethra, ureter) or man-made passageways in a patient. The antenna 102 and cable 104 are flexible, whereby the same may assume a tortuous path upon insertion into the pancreatic duct 108.

Preferably, the dielectric material 100 is resilient in order to permit flexing of the antenna 102 and cable 104, and return of the same to their original configuration. Any suitable dielectric material having the properties required to function in this environment may be employed. In general, it is preferred that the antenna 102 and cable 104 be covered by about 5 to about 100 microns of such material. A suitable dielectric may, for example, be a bio-compatible plastic material, or blend having the desired properties. The dielectric material employed may, for example, be tetrafluoroethylene, which is sold under the trade designation, "Teflon." It is known for its fine electrical insulating properties, does not interact with any components in water, and can be safely used in blood vessels. The purpose of the dielectric material 100 is to provide biocompatibility. However, a relatively thick insulation (e.g., greater than about 0.1 mm) will improve SNR at the cost of thickening the antenna 102 and cable 104.

It will be appreciated that the antenna 102, cable 104 and suitable impedance matching circuit are employable with other specimens. For example, the image of the aorta of a live rabbit (not shown) may be obtained. The antenna 102 and cable 104 may be inserted from the femoral artery of the rabbit. Although the rabbit femoral artery is typically very small (e.g., approximately about 1 mm in diameter), catheter-like insertion is easily performed with the exemplary antenna 102 and cable 104.

Any suitable method, such as X-ray fluoroscopic imaging, may be employed to confirm the placement of the antenna 102 in the specimen. It will be appreciated that the placement of the antenna 102 may also be confirmed by a wide variety of other imaging methods. It will further be appreciated that the insertion of the antenna 102 into the patient may be accomplished by direct insertion of the antenna 102 and cable 104 into a suitable blood vessel, by insertion through a catheter guide, and by a wide variety of insertion methods.

Figure 10:
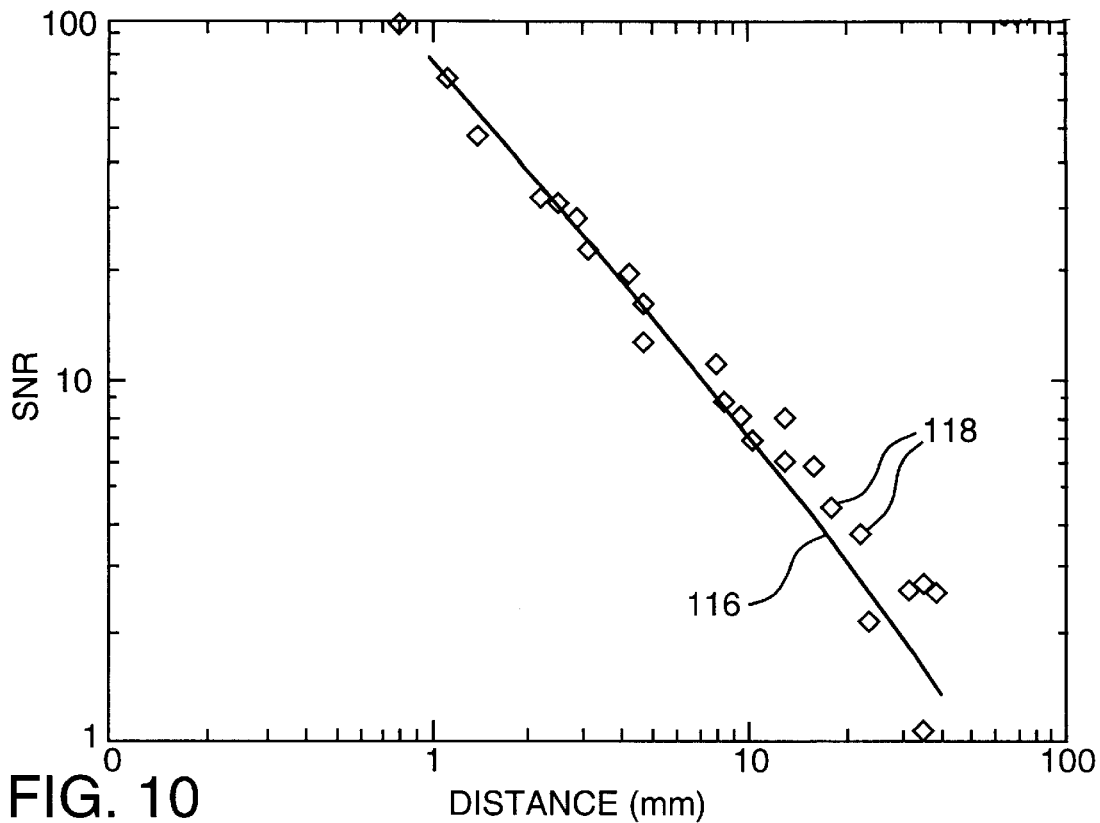
FIG. 10 is a log-log plot of measured and theoretical signal-to-noise ratio with respect to radial distance from the loopless antenna of FIG. 4.

FIG. 10 is a log-log plot of theoretical SNR (shown as a line 116) and measured SNR (shown as discrete diamonds 118) with respect to radial distance from the longitudinal axis 48 of the antenna 27 of FIG. 4. For example, pulse sequences may be employed which allow a voxel size of 0.16×0.16×1.5 mm. Images may be acquired with an 8 cm FOV, 512×512 data acquisition matrix, 1.5 mm slice thickness, 2 NEX, and 16 KHz receiver bandwidth. Such imaging parameters correspond to an effective pixel bandwidth of 0.06 Hz and permit 12 slices of similar images to be obtained in about ten minutes.

The exemplary antenna 27 and cable 29 of FIG. 4, and suitable matching circuit provide a relatively high resolution of the specimen, such as human tissue, to a radial distance of about 10 mm from the longitudinal axis 48, and can be employed to image to radial distances of about 20 mm or greater. Near-microscopic resolution can be obtained in the immediate vicinity of the antenna 27. Increasing the main magnetic field strength improves the resolution significantly and enables imaging with smaller voxel volume.

Figure 11:
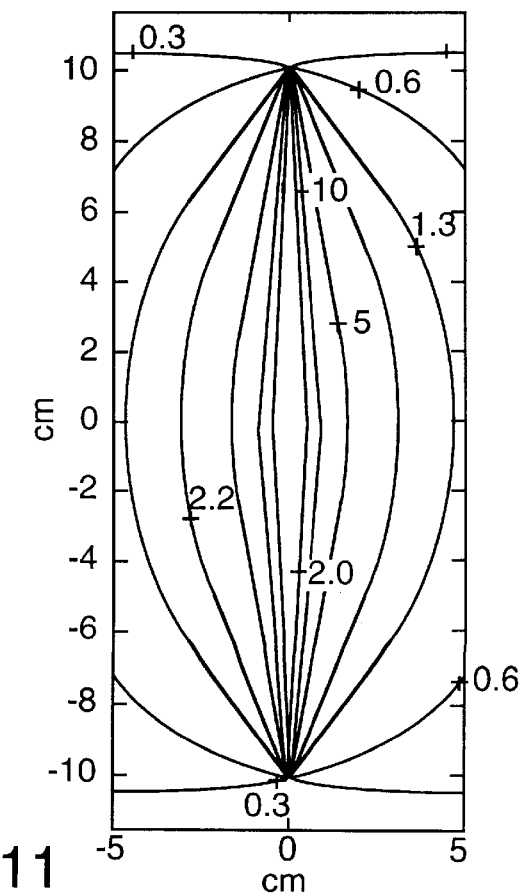
FIG. 11 is a contour plot of theoretical SNR as calculated for a balanced loopless antenna.

FIG. 11 is a contour plot of theoretical SNR as calculated for a balanced loopless antenna similar to the antenna 27 of FIG. 4. The calculation assumes that pulse sequences are employed at 1.5 T main magnetic field strength, with a 160×160×1500 micron voxel size and an effective pixel bandwidth of 0.06 Hz. The units on the horizontal and vertical axes are in centimeters. The balanced loopless antenna is situated in the center of the plot at 0 cm of the horizontal axis and extends from −10 cm to 10 cm of the vertical axis.

Figure 12:
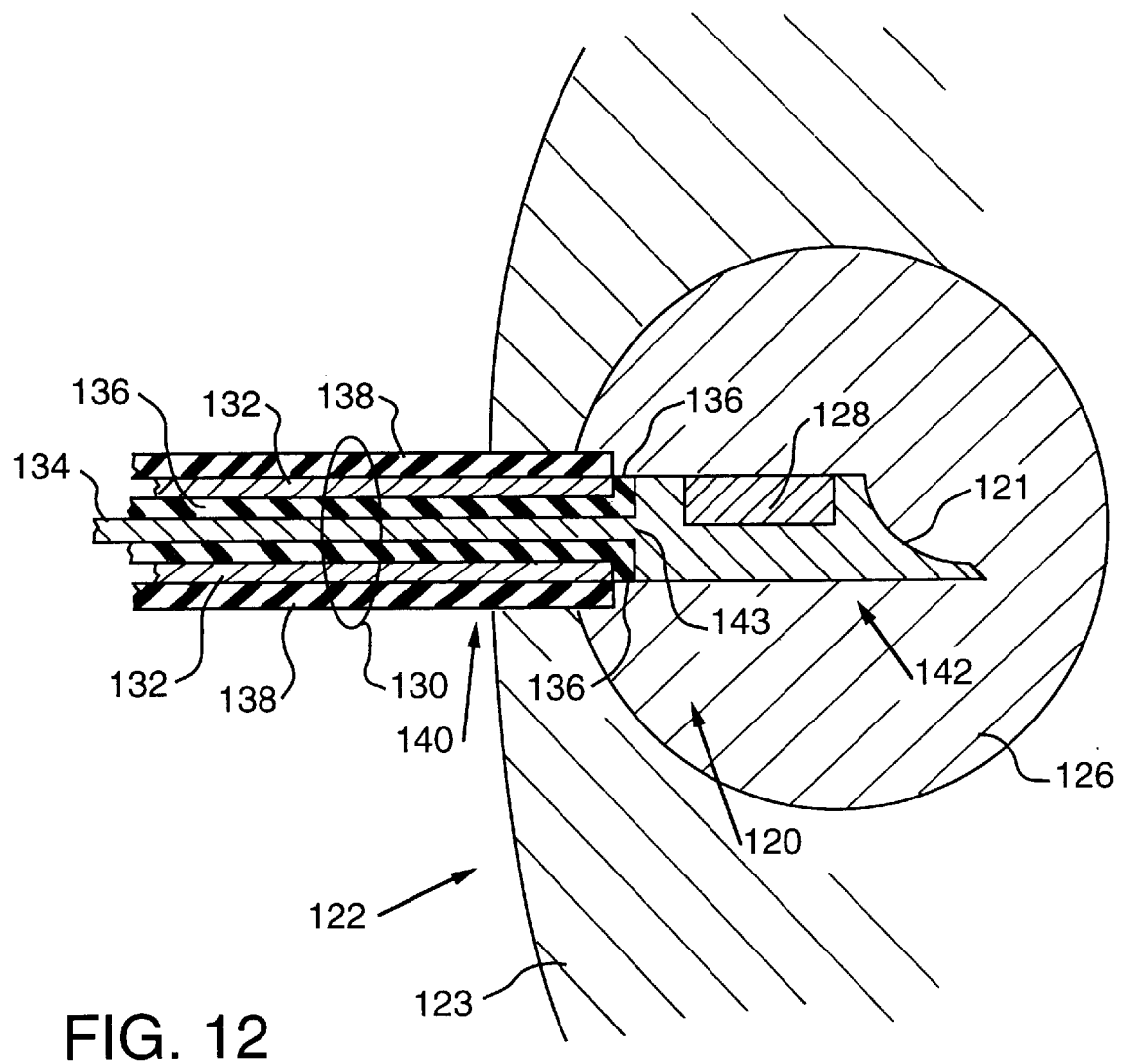
FIG. 12 is a schematic cross-sectional illustration showing a loopless antenna of the present invention employed as a biopsy needle.

Referring to FIG. 12, another specific example of the antenna 27' of FIG. 3 of the invention will be considered.

EXAMPLE 6

FIG. 12 is a schematic cross-sectional illustration showing a loopless antenna 120 of the present invention in the form of a biopsy needle 121. The antenna 120 is employed in vivo on a patient 122. The body 123 of the patient 122 contains a lesion 126. The antenna 120 serves to image the lesion 126 in vivo before a sample 128 of the lesion 126 is taken by the biopsy needle 121. This enables more accurate biopsy needle positioning.

The antenna 120 is formed at the end of a coaxial cable 130 having an outer shield 132 and an inner conductor 134 which is electrically insulated from such shield 132 by a dielectric portion 136. The biopsy needle 121 can slide inside a non-conducting conducting sheath 138. The antenna 120 has a first pole 140 formed by the shield 132, and a second pole 142 formed by the biopsy needle 121 which is electrically connected to the portion 143 of the inner conductor 134, and which is electrically insulated from the shield 132 by the dielectric portion 136. The antenna 120, coaxial cable 130 and biopsy needle 121 are composed of materials which are magnetic resonance compatible, such as a conductors or dielectric insulators as distinguished from a steel material, for example. The end of the coaxial cable 130 opposite the biopsy needle 121 is preferably electrically interconnected with a suitable impedance matching circuit such as one of the circuits 50 and 66 of FIGS. 6 and 7, respectively.

Figure 13:
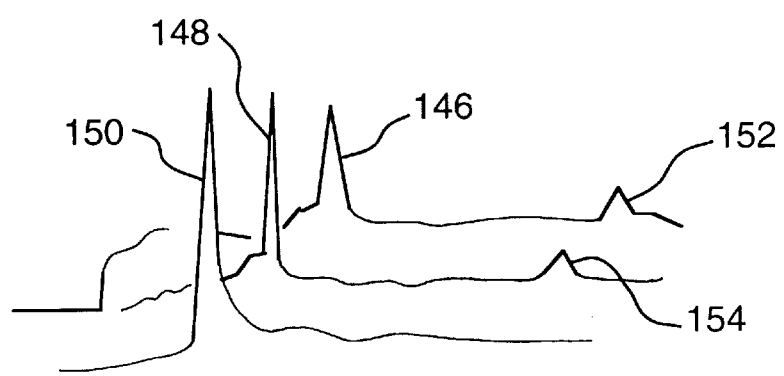
FIG. 13 is a representation of the spectra of three adjacent voxels along the length of the catheter coil of FIG. 2.

FIG. 13 is a representation of the spectra of three adjacent voxels along the length of the catheter coil 18 of FIG. 2 which are established by the computer 12 of FIG. 1 to determine the chemical shift spectra at those locations. It is believed that a comparable spectra may be acquired along the length of the loopless antenna 27 of FIG. 4. The spectra of three adjacent voxels is shown in FIG. 13 with peaks 146,148,150 representing water signals from the three regions and peaks 152,154 from lipid signals in or adjacent to the region of interest, such as blood vessel walls. Water and lipid peaks will tend to vary between normal and atherosclerotic vessels.

Figure 14:
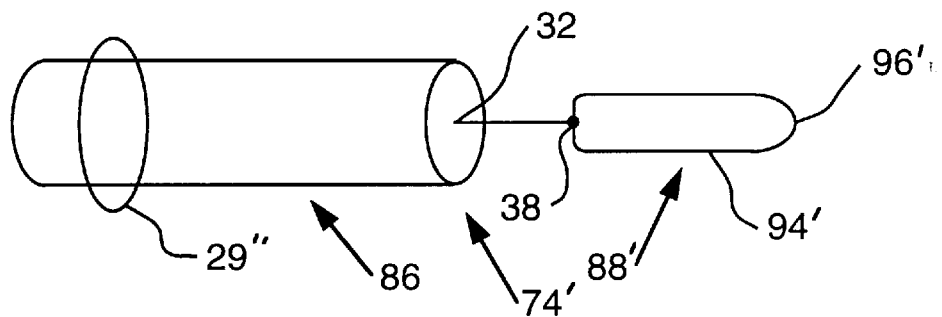
FIG. 14 is a cross-sectional view of another embodiment of a dipole antenna.

Referring to FIG. 14, a specific example of the antenna 27' of the invention will be considered.

EXAMPLE 7

FIG. 14 is a cross-sectional view of a coaxial cable 29" and a dipole antenna 74' similar to the loopless antenna 74 of FIG. 8. The dipole antenna 74' has a first pole 86 and a second pole 88'. The second pole 88' includes a mechanical loop conductor 94' electrically interconnected with the portion 38 of the inner conductor 32. Preferably, for use in a patient, the end 96' of the mechanical loop conductor 94' is suitably rounded to obviate damaging a patient (not shown). The exemplary mechanical loop conductor 94' has a generally oval shape, although the invention is applicable to any shape which is electrically isolated from the first pole 86. This is contrasted with the conventional catheter coil 18 of FIG. 2 in which one of the conductors 19,20 may be connected to a coaxial cable shield and the other conductor may be connected to a coaxial cable inner conductor, thereby forming an electrical loop.

Figure 15:
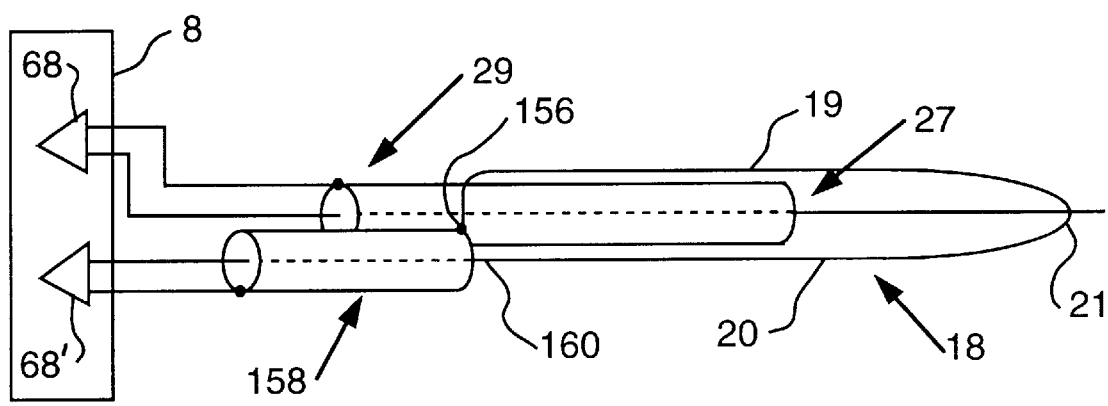
FIG. 15 is a schematic illustration of a loopless antenna employed in combination with a catheter coil.

Referring to FIG. 15, a specific example of the antenna 27' of the invention will be considered.

EXAMPLE 8

FIG. 15 is a schematic illustration of the loopless antenna 27 employed in combination with the catheter coil 18 of FIG. 2. The conductor 19 of the catheter coil 18 is connected to outer shield 156 of coaxial cable 158 and the conductor 20 is connected to inner conductor 160 thereby forming an electrical loop. Also referring to FIG. 1, the coaxial cable 158 is connected to one preamplifier 68' of the receiver 8. The coaxial cable 29 of the loopless antenna 27 is connected to another preamplifier 68 of the receiver 8. Both the coil 18 and the antenna 27 receive MR signals and emit corresponding output signals which are converted by the converter 10 and are received and processed by the computer 12 in order to combine the same into MR information for display by the CRT 16. Preferably, the coil 18 and the antenna 27 are mounted coaxially in order to facilitate use of the better SNR performance of the coil 18 at relatively small distances from the common axis and the better SNR performance of the loopless antenna 27 at relatively large distances therefrom. It will be appreciated that other types and number of coils may be employed with the preamplifier 68' (e.g., two back-to-back solenoid coils, a pair of quadrature coils) in combination with the antenna 27.

The exemplary antennas 27,74,120 disclosed herein increase SNR and provide suitable resolution in MR imaging of blood vessels. The sensitivity of the antennas 27,74, 120 decays approximately as the inverse of the radial distance from the antenna longitudinal axis. Hence, it provides useful SNR in a cylindrical volume around such antennas. The antennas 27,74,120 allow electronic circuits to be placed outside the body and can be easily constructed to a very thin diameter which obviates the size and mechanical property restrictions of catheter coils. The physical dimensions of the antennas 27,74 make it practical for insertion into blood vessels. The antennas 27,74,120 have a low quality factor (Q) and, hence, do not require appreciable tuning when inserted in non-linear intravascular systems.

The simple structure of the antennas 27,74 makes it possible to construct and operate these devices in a reliable manner in various imaging techniques, such as multislice MRI, 3-D MRI, or 1-D spectroscopy, and in various interventional techniques on a wide variety of specimens. The exemplary loopless antenna 120 and MR compatible biopsy needle 121 facilitate the same in addition to providing the capability of conducting imaging before a biopsy sample is removed from a patient.

Pathogenesis of a blood vessel wall due to atherosclerosis is difficult to characterize by conventional techniques which only investigate the vascular lumen. Intravascular MRI has the unique potential to characterize all three layers of the vessel wall, plaque extent, and composition, as well as thickness and extent of the fibrous cap. The goal of high resolution imaging of atherosclerotic plaques can only be achieved by increasing the SNR of the acquired images. The exemplary antennas 27,74 greatly increase sensitivity to the target plaque.

The development of new MRI scanners has led to interventional possibilities which will benefit from the intravascular loopless antennas 27,74. Interventional techniques for atherosclerotic disease may be monitored using real-time, high resolution MR imaging techniques. In addition to precise guidance of laser angioplasty and atherectomy procedures, these apparatus and methods may be used to fully stage lesions and serve as an experimental tool in assessing new therapeutic applications to atherosclerotic disease. Furthermore, with the resulting intravascular MR imaging system, reliable diagnostic information on atherosclerosis may be obtained and MR-guided interventions may be performed with high precision.

It will be appreciated, therefore, that the present invention provides an improved method and associated apparatus for enhanced MR imaging and 1-D chemical shift analysis of the interior of a specimen. The loopless antenna 74 provides a generally uniform sensitivity along the longitudinal axis of the dipoles 86,88 and, as a result of the use of such antenna, facilitates a longer portion of the specimen being imaged with one antenna position. Further, no tuning is required after insertion of the antennas 27,74,120 into a specimen. These antennas, in addition to serving solely as a receiver antenna in one embodiment, may in another embodiment function as a transmitter antenna and a receiver antenna. The invention may be employed generally simultaneously with medical intervention, such as, for example, laser removal of blood vessel plaque.

The invention also contemplates enhanced efficiency through the use of at least one of a balancing transformer and an impedance matching circuit.

While for clarity of disclosure reference has been made herein to display means for displaying an image, it will be appreciated that the image information may be stored, printed on hard copy, be computer modified, or be combined with other data. All such processing shall be deemed to fall within the terms "display" or "displaying" as employed herein.

Whereas particular embodiments of the present invention have been described herein for purposes of illustration, it will be appreciated by those skilled in the art that numerous variations of the details may be made without departing from the invention as described in the appended claims.

We claim:

1. A method of magnetic resonance analysis of a specimen, said method comprising
   positioning said specimen within a main magnetic field,
   introducing a loopless antenna in close proximity to said specimen,
   imposing said main magnetic field on a region of interest of said specimen,
   applying radio frequency pulses to said region of interest to excite magnetic resonance signals within said specimen,
   applying gradient magnetic pulses to said region of interest to spatially encode said magnetic resonance signals,
   employing a coaxial cable with an outer shield and an inner conductor,
   employing a portion of said outer shield and a portion of said inner conductor as an antenna portion of said loopless antenna for receiving said magnetic resonance signals and employing another portion of said coaxial cable for emitting responsive output signals,
   employing processing means for receiving and processing said responsive output signals and converting them into magnetic resonance information, and
   employing display means for receiving said magnetic resonance information from said processing means and displaying the same as an image or as chemical shift spectra.

2. The method of claim 1 including
   employing a dipole antenna portion of said loopless antenna for receiving said magnetic resonance signals, and
   employing said another portion of said coaxial cable as a connection portion for emitting said responsive output signals.

3. The method of claim 2 including
   employing said antenna portion having a length of about 3 cm to about 20 cm, and having a maximum width of about 0.3 mm to about 1.0 cm.

4. The method of claim 1 including
   employing said processing means to convert said responsive output signals into image information, and
   employing said display means to receive and display said image information.

5. The method of claim 1 including
   including in said responsive output signals spatially localized chemical shift information,
   employing said processing means to convert said chemical shift information into chemical shift spectra, and
   employing said display means to receive and display said chemical shift spectra.

6. The method of claim 1 including
   employing an impedance matching circuit electrically interposed between said loopless antenna and said processing means to enhance radio frequency power transfer and magnetic resonance signal-to-noise ratio from said loopless antenna to said processing means.

7. The method of claim 6 including
   employing said coaxial cable as a first coaxial cable,
   employing a second coaxial cable electrically interposed between said processing means and said impedance matching circuit, and
   said impedance matching circuit matching the impedance of said loopless antenna to the impedance of said second coaxial cable.

8. The method of claim 7 including
   employing said coaxial cable with an inner conductor and an outer shield, and
   employing a matching capacitor in said impedance matching circuit electrically interposed between said inner conductor and said outer shield.

9. The method of claim 8 including
   employing diode means electrically interposed between said impedance matching circuit and said processing means, and
   employing a blocking capacitor in said impedance matching circuit electrically interposed between said diode means and said loopless antenna.

10. The method of claim 9 including
    employing said blocking capacitor electrically interposed between said diode means and said matching capacitor.

11. The method of claim 1 including
    employing said responsive output signals as first responsive output signals,
    employing at least one receiver coil with said loopless antenna,
    said receiver coil receiving said magnetic resonance signals and emitting second responsive output signals, and
    employing said processing means for receiving and processing said first and second responsive output signals and combining them into said magnetic resonance information.

12. The method of claim 1 including
    employing said antenna portion with a maximum width of about 0.3 mm to about 1.0 cm.

13. The method of claim 1 including
    employing said loopless antenna as an invasive probe, and
    delivering said invasive probe into a blood vessel of a patient.

14. The method of claim 13 including
    inserting said invasive probe within blood vessels to acquire magnetic resonance image information thereof.

15. The method of claim 13 including
    inserting said invasive probe within blood vessels to acquire magnetic resonance chemical shift spectra or magnetic resonance image information thereof.

16. The method of claim 13 including
    employing said method generally simultaneous with an interventional procedure on the patient.

17. The method of claim 1 including
    employing said loopless antenna in vivo in a patient.

18. The method of claim 17 including
    employing said loopless antenna in a human being.

19. The method of claim 1 including
    employing said loopless antenna as a magnetic resonance biopsy needle.

20. The method of claim 1 including
    employing a patient as said specimen, and performing generally simultaneously with said magnetic resonance analysis a medical procedure on said patient.

21. The method of claim 1 including
employing said loopless antenna in multislice imaging of said specimen without requiring movement of said loopless antenna.

22. The method of claim 1 including
employing computer means as said processing means.

23. The method of claim 1 including
employing said method in vitro on a specimen which has been removed from a patient.

24. The method of claim 1 including
employing said method substantially simultaneously with surgical procedures on a patient.

25. The method of claim 1 including
employing said loopless antenna as a radio frequency pulse transmitting source in addition to employment as a receiver antenna.

26. The method of claim 1 including
employing said loopless antenna as an invasive probe, and
introducing said invasive probe into said specimen to conduct internal magnetic resonance analysis thereof.

27. The method of claim 1 including
employing said loopless antenna as an invasive probe, and
introducing said invasive probe into said specimen to conduct internal magnetic resonance analysis thereof.

28. The method of claim 1 including
electrically connecting a magnetic resonance biopsy needle to said portion of said inner conductor.

29. The method of claim 1 including
said antenna portion and said coaxial cable having a combined length of up to about 2 m.

30. A method of magnetic resonance analysis of a specimen, said method comprising
positioning said specimen within a main magnetic field,
introducing an antenna in close proximity to said specimen,
employing as said antenna a loopless antenna,
imposing said main magnetic field on a region of interest of said specimen,
applying radio frequency pulses to said region of interest to excite magnetic resonance signals within said specimen,
applying gradient magnetic pulses to said region of interest to spatially encode said magnetic resonance signals,
said antenna receiving said magnetic resonance signals and emitting responsive output signals,
employing processing means for receiving and processing said responsive output signals and converting them into magnetic resonance information,
employing display means for receiving said magnetic resonance information from said processing means and displaying the same as an image or as chemical shift spectra,
employing said antenna as a magnetic resonance biopsy needle,
employing a coaxial cable with said antenna, with said coaxial cable having an outer shield and an inner conductor, and
employing said inner conductor as said biopsy needle.

31. A method of magnetic resonance analysis of a specimen, said method comprising
positioning said specimen within a main magnetic field,
introducing an antenna in close proximity to said specimen,
employing as said antenna a loopless antenna,
imposing said main magnetic field on a region of interest of said specimen,
applying radio frequency pulses to said region of interest to excite magnetic resonance signals within said specimen,
applying gradient magnetic pulses to said region of interest to spatially encode said magnetic resonance signals,
said antenna receiving said magnetic resonance signals and emitting responsive output signals,
employing processing means for receiving and processing said responsive output signals and converting them into magnetic resonance information,
employing display means for receiving said magnetic resonance information from said processing means and displaying the same as an image or as chemical shift spectra,
employing a dipole antenna portion of said loopless antenna for receiving said magnetic resonance signals,
employing a connection portion of said loopless antenna for emitting said responsive output signals,
employing said antenna as an invasive probe,
introducing said invasive probe into said specimen to conduct internal magnetic resonance analysis thereof,
employing a coaxial cable with an outer shield and an inner conductor, and
employing a portion of said outer shield and a portion of said inner conductor as said dipole antenna portion of said loopless antenna for receiving said magnetic resonance signals.

32. The method of claim 31 including
employing said portion of said outer shield operatively associated with a first pole of said loopless antenna, and
employing said portion of said inner conductor operatively associated with a second pole of said loopless antenna.

33. The method of claim 32 including
employing balancing transformer means operatively associated with said portion of said outer shield.

34. The method of claim 33 including
delivering said antenna into a blood vessel, and
employing an insulator in said balancing transformer means with a dielectric constant about equal to a dielectric constant of blood in said blood vessel.

35. A method of magnetic resonance analysis of a specimen, said method comprising
positioning said specimen within a main magnetic field,
introducing an antenna in close proximity to said specimen,
employing as said antenna a loopless antenna,
imposing said main magnetic field on a region of interest of said specimen,
applying radio frequency pulses to said region of interest to excite magnetic resonance signals within said specimen,
applying gradient magnetic pulses to said region of interest to spatially encode said magnetic resonance signals,
said antenna receiving said magnetic resonance signals and emitting responsive output signals,
employing processing means for receiving and processing said responsive output signals and converting them into magnetic resonance information, employing display means for receiving said magnetic resonance information from said processing means and displaying the same as an image or as chemical shift spectra, employing a dipole antenna portion of said loopless antenna for receiving said magnetic resonance signals, employing a connection portion of said loopless antenna for emitting said responsive output signals, employing a coaxial cable as said connection portion of said loopless antenna for emitting said responsive output signals, employing said coaxial cable with an outer shield and an inner conductor, employing said outer shield as a first pole of said loopless antenna, and employing said inner conductor as a second pole of said loopless antenna.

36. The method of claim 35 including employing said antenna with a length of up to about 2 m.

37. Magnetic resonance analysis apparatus for a specimen, said apparatus comprising magnetic field generating means for establishing a main magnetic field on said specimen, magnetic field gradient generating means for establishing gradients in said main magnetic field, radio frequency signal generating means for emitting pulsed radio frequency signals to at least portions of said specimen disposed within said main magnetic field, a loopless antenna assembly comprising a coaxial cable having an outer shield and an inner conductor, with a portion of said outer shield and a portion of said inner conductor of said coaxial cable forming an antenna portion of said loopless antenna assembly at least for receiving signals emitted from said specimen responsive to said pulsed radio frequency signals, and with another portion of said coaxial cable for emitting responsive output signals, processing means for receiving and processing said responsive output signals from said loopless antenna assembly and creating magnetic resonance information related thereto, and display means for displaying said magnetic resonance information received from said processing means as an image or as chemical shift spectra.

38. The apparatus of claim 37 including said loopless antenna is a dipole antenna.

39. The apparatus of claim 38 including said dipole antenna is inserted in said specimen, and said magnetic field gradient generating means generating a magnetic field gradient over a region of interest of said specimen in order to generate spatially resolved chemical shift spectra in the region of interest in said specimen.

40. The apparatus of claim 37 including said loopless antenna is a dipole antenna having an external diameter structured to be received within a blood vessel of a patient, said processing means converting said responsive output signals into magnetic resonance spectroscopic information or magnetic resonance image information, and said display means displaying said magnetic resonance spectroscopic information or said magnetic resonance image information in order to image said blood vessel.

41. The apparatus of claim 37 including said antenna portion is flexible, whereby the same may assume a tortuous path upon insertion into said specimen.

42. The apparatus of claim 37 including said loopless antenna is a dipole antenna, said antenna portion is a dipole antenna portion, said dipole antenna portion having a length of about 3 cm to about 20 cm, and said dipole antenna portion having a maximum width of about 0.3 mm to about 1.0 cm.

43. The apparatus of claim 37 including said antenna portion is structured to be received within a naturally occurring passageway in a human being.

44. The apparatus of claim 37 including said antenna portion is structured as an invasive probe and is introduced into said specimen to conduct internal magnetic resonance analysis thereof.

45. The apparatus of claim 37 including said loopless antenna is a dipole antenna, said antenna portion is a dipole antenna portion for receiving said signals emitted from said specimen responsive to said pulsed radio frequency signals, and said coaxial cable having a connection portion for emitting said responsive output signals.

46. The apparatus of claim 37 including said processing means including impedance matching means electrically interposed between said coaxial cable and said processing means for enhancing radio frequency power transfer and magnetic resonance signal-to-noise ratio from said antenna portion to said processing means.

47. The apparatus of claim 46 including said coaxial cable means electrically interposed between said loopless antenna and said impedance matching means.

48. The apparatus of claim 46 including said loopless antenna and said coaxial cable means each having an external diameter structured to be received within at least one of a pancreatic duct, a bile duct, a urethra, and a ureter of a patient.

49. The apparatus of claim 46 including said specimen is a blood vessel of a patient, said antenna portion is positionable within said blood vessel, and said impedance matching means is positionable external to said blood vessel.

50. The apparatus of claim 49 including said antenna portion having a length of about 3 cm to about 20 cm, and a maximum width of about 0.3 mm to about 1.0 cm.

51. The apparatus of claim 37 including said antenna portion having a length which facilitates multislice imaging without moving said antenna portion.

52. The apparatus of claim 37 including said radio frequency signal generating means also having means for sourcing radio frequency pulses to said antenna portion, and said antenna portion also for transmitting said radio frequency pulses in order to excite magnetic resonance signals.

53. The apparatus of claim 37 including said loopless antenna is a dipole antenna structured as a biopsy needle.

54. The apparatus of claim 37 including
said loopless antenna is a dipole antenna, and
said dipole antenna having a length of about 3 cm to about 20 cm.

55. The apparatus of claim 37 including
said outer shield having an outer surface, an inner surface, and balancing transformer means for impeding current flow on said outer surface without significantly impeding current flow on said inner surface.

56. The apparatus of claim 37 including
said coaxial cable having a dielectric portion which electrically insulates said inner conductor from said outer shield, and
a biopsy needle is electrically connected to said portion of said inner conductor and is electrically insulated from said outer shield by the dielectric portion.

57. Magnetic resonance analysis apparatus for a specimen, said apparatus comprising
magnetic field generating means for establishing a main magnetic field on said specimen,
magnetic field gradient generating means for establishing gradients in said main magnetic field,
radio frequency signal generating means for emitting pulsed radio frequency signals to at least portions of said specimen disposed within said main magnetic field,
antenna means having a loopless antenna at least for receiving signals emitted from said specimen responsive to said pulsed radio frequency signals and emitting responsive output signals,
said loopless antenna is a dipole antenna having a first pole and a second pole,
processing means for receiving and processing said responsive output signals from said antenna means and creating magnetic resonance information related thereto,
display means for displaying said magnetic resonance information received from said processing means as an image or as chemical shift spectra,
said antenna means including impedance matching means electrically interposed between said loopless antenna and said processing means for enhancing radio frequency power transfer and magnetic resonance signal-to-noise ratio from said loopless antenna to said processing means, and said antenna means also including coaxial cable means for emitting said responsive output signals, with said coaxial cable means electrically interposed between said loopless antenna and said impedance matching means,
said coaxial cable means having an outer shield and an inner conductor,
said outer shield having a portion thereof operatively associated with said first pole of said dipole antenna, and
said inner conductor having a portion thereof operatively associated with said second pole of said dipole antenna.

58. The apparatus of claim 57 including
said portion of said outer shield operatively associated with said first pole having an inner primary shield and an outer secondary shield, with each of said inner primary shield and said outer secondary shield being coaxial with said inner conductor, and
said coaxial cable means also having an insulator between said inner primary shield and said outer secondary shield, with said insulator, said inner primary shield and said outer secondary shield forming a balancing transformer means operatively associated with said first pole.

59. The apparatus of claim 58 including
said coaxial cable means having an external diameter structured to be received within a blood vessel of a patient, and
said balancing transformer means having an insulator with a dielectric constant about equal to a dielectric constant of blood in said blood vessel.

60. Magnetic resonance analysis apparatus for a specimen, said apparatus comprising
magnetic field generating means for establishing a main magnetic field on said specimen,
magnetic field gradient generating means for establishing gradients in said main magnetic field,
radio frequency signal generating means for emitting pulsed radio frequency signals to at least portions of said specimen disposed within said main magnetic field,
antenna means having a loopless antenna at least for receiving signals emitted from said specimen responsive to said pulsed radio frequency signals and emitting responsive output signals, said loopless antenna is a dipole antenna having a first pole and a second pole, said antenna means also including coaxial cable means for emitting said responsive output signals, said coaxial cable means having an outer shield, and said outer shield having balancing transformer means operatively associated with said first pole,
processing means for receiving and processing said responsive output signals from said antenna means and creating magnetic resonance information related thereto, and
display means for displaying said magnetic resonance information received from said processing means as an image or as chemical shift spectra.

61. Magnetic resonance analysis apparatus for a specimen, said apparatus comprising
magnetic field generating means for establishing a main magnetic field on said specimen,
magnetic field gradient generating means for establishing gradients in said main magnetic field,
radio frequency signal generating means for emitting pulsed radio frequency signals to at least portions of said specimen disposed within said main magnetic field,
antenna means having a loopless antenna at least for receiving signals emitted from said specimen responsive to said pulsed radio frequency signals and emitting responsive output signals, said loopless antenna is a dipole antenna having a first pole and a second pole,
processing means for receiving and processing said responsive output signals from said antenna means and creating magnetic resonance information related thereto,
display means for displaying said magnetic resonance information received from said processing means as an image or as chemical shift spectra,
said antenna means including impedance matching means electrically interposed between said loopless antenna and said processing means for enhancing radio frequency power transfer and magnetic resonance signal-to-noise ratio from said loopless antenna to said processing means, and said antenna means also including coaxial cable means for emitting said responsive output signals, with said coaxial cable means electrically interposed between said loopless antenna and said impedance matching means, said coaxial cable means having an outer shield and an inner conductor, with said outer shield as the first pole of said loopless antenna and said inner conductor as the second pole of said loopless antenna.

62. The apparatus of claim 61 including said dipole antenna and said coaxial cable means having a length of up to about 2 m.

63. A magnetic resonance loopless antenna assembly comprising a coaxial cable having an outer shield and an inner conductor, with a portion of said outer shield and a portion of said inner conductor forming an antenna portion of said loopless antenna assembly, said antenna portion at least for receiving magnetic resonance signals emitted from a specimen, with another portion of said coaxial cable for emitting responsive output signals.

64. The loopless antenna assembly of claim 63 including said antenna portion is resiliently flexible.

65. The loopless antenna assembly of claim 63 including said antenna portion and said coaxial cable having a combined length of up to about 2 m.

66. The loopless antenna assembly of claim 63 including said antenna portion has a cylindrical conductor electrically interconnected with said portion of said inner conductor.

67. The loopless antenna assembly of claim 63 including said portion of said outer shield having an inner primary shield and an outer secondary shield, with each of said inner primary shield and said outer secondary shield being coaxial with said inner conductor, and said coaxial cable also having an electrical insulator between said inner primary shield and said outer secondary shield, with said insulator, said inner primary shield and said outer secondary shield forming balancing transformer means.

68. The loopless antenna assembly of claim 67 including said coaxial cable having an external diameter structured to be received within a blood vessel of a patient, and said insulator having a dielectric constant about equal to a dielectric constant of blood in said blood vessel.

69. A magnetic resonance antenna assembly comprising an antenna having loopless antenna means at least for receiving magnetic resonance signals emitted from a specimen and emitting responsive output signals, said loopless antenna means is a dipole antenna having a first pole and a second pole, said antenna also having a coaxial cable, with said coaxial cable having an outer shield and an inner conductor for emitting said responsive output signals, said outer shield having a portion thereof operatively associated with said first pole, and said inner conductor having a portion thereof operatively associated with said second pole.

70. The antenna assembly of claim 69 including said portion of said outer shield operatively associated with said first pole having an inner primary shield and an outer secondary shield, with each of said inner primary shield and said outer secondary shield being coaxial with said inner conductor, and said coaxial cable also having an insulator between said inner primary shield and said outer secondary shield, with said insulator, said inner primary shield and said outer secondary shield forming a balancing transformer means operatively associated with said first pole.

71. The antenna assembly of claim 70 including said coaxial cable having an external diameter structured to be received within a blood vessel of a patient, and said insulator having a dielectric constant about equal to a dielectric constant of blood in said blood vessel.

72. A magnetic resonance antenna assembly comprising an antenna having loopless antenna means at least for receiving magnetic resonance signals emitted from a specimen and emitting responsive output signals, said loopless antenna means is a dipole antenna having a first pole and a second pole, said antenna also having a coaxial cable, with said coaxial cable having an outer shield and an inner conductor for emitting said responsive output signals, with said outer shield as the first pole of said loopless antenna means and said inner conductor as the second pole of said loopless antenna means.

73. The antenna assembly of claim 72 including said antenna having a length of up to about 2 m.

* * * * *